United States Patent [19]

Brooks et al.

[11] Patent Number: 5,756,531
[45] Date of Patent: May 26, 1998

[54] IMINOXY DERIVATIVES OF INDOLE AND INDENE COMPOUNDS AS INHIBITORS OF PROSTAGLANDIN BIOSYNTHESIS

[75] Inventors: Clint D. W. Brooks, Libertyville, Ill.; Richard A. Craig, Racine, Wis.; David E. Gunn, Hamden, Conn.; Teodozyji Kolasa, Lake Villa, Ill.; Jimmie L. Moore, Gurnee, Ill.; Andrew O. Stewart, Libertyville, Ill.

[73] Assignee: Abbott Laboratories, Abbott Park, Ill.

[21] Appl. No.: 640,271

[22] Filed: Apr. 30, 1996

[51] Int. Cl.$^6$ .............. C07D 209/12; C07D 209/14; A61K 31/40; A61K 31/405
[52] U.S. Cl. .............. 514/408; 514/415; 514/428; 548/469; 548/491; 548/505; 548/507; 548/509; 548/511; 548/562; 564/253; 564/254; 564/265; 564/266
[58] Field of Search .............. 514/408, 415, 514/427, 428; 548/469, 511, 516, 556, 560, 562

[56] References Cited

U.S. PATENT DOCUMENTS 5,399,699  3/1995  Kolasa et al. .............. 546/174

FOREIGN PATENT DOCUMENTS 9203132  3/1992  WIPO .

OTHER PUBLICATIONS

J. A. Mitchell et al., "Cyclooxygenase-2: Regulatory and Relevance in Inflammation," *Biochemical Pharmacology*, vol. 50, No. 10 (1995), 1535–1542.

B. Battistini et al., Cox–1 and Cox–2: Toward the Development of More Selective NSAIDs, *Drug News and Perspectives*, vol. 7, No. 8 (1994) 501–512.

D. L. DeWitt et al., "The Differential of Prostaglandin Endoperoxide H Synthases–1 and –2 to Nonsteroidal Anti–Inflammatory Drugs: Aspirin Derivatives as Selective Inhibitors," *Medicinal Chemistry Research*, vol. 5, No. 5 (1995) 325–343.

PCT International Search Report Corresponding to PCT/US97/04981.

*Primary Examiner*—Johann Richter
*Assistant Examiner*—Jane C. Oswecki
*Attorney, Agent, or Firm*—Frank Z. Yang

[57] ABSTRACT

The present invention provides a class of substituted indole and indene iminoxy derivatives of the formula

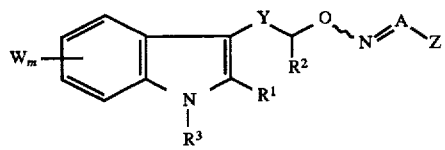

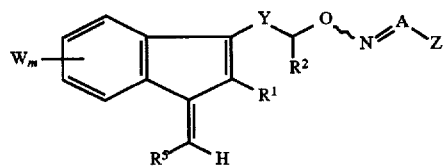

and

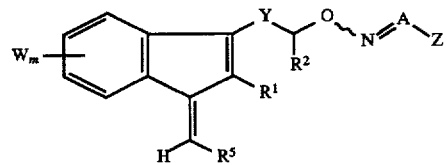

which inhibit leukotriene biosynthesis and are useful in the treatment of allergic and inflammatory disease states.

9 Claims, No Drawings

IMINOXY DERIVATIVES OF INDOLE AND INDENE COMPOUNDS AS INHIBITORS OF PROSTAGLANDIN BIOSYNTHESIS

TECHNICAL FIELD

This invention relates to novel compounds having activity to inhibit prostaglandin biosynthesis, to pharmaceutical compositions comprising these compounds and to a medical method of treatment. More particularly, this invention concerns iminoxy containing derivatives of indole and indene compounds which inhibit prostaglandin biosynthesis particularly the induced prostaglandin endoperoxide H synthase (PGHS-2), cyclooxygenase-2 (COX-2), to pharmaceutical compositions comprising these compounds and to a method of inhibiting leukotriene biosynthesis.

BACKGROUND OF THE INVENTION

The prostaglandins are extremely potent substances which produce a wide variety of biological effects, often in the nanomolar to picomolar concentration range. The discovery of two forms of prostaglandin endoperoxide H synthase-1 and -2 (PGHS-1 and PGHS-2) that catalyze the oxidation of arachidonic acid leading to prostaglandin biosynthesis has resulted in renewed research to delineate the role of these two isozymes in physiology and pathophysiology. These isozymes have been shown to have different gene regulation and represent distinctly different prostaglandin biosynthesis pathways. The PGHS-1 pathway is expressed constitutively in most cell types. It responds to produce prostaglandins that regulate acute events in vascular homeostasis and also has a role in maintaining normal stomach and renal function. The newly discovery PGHS-2 pathway involves an induction mechanism which has been liked to inflammation, mitogenesis and ovulation phenomena.

Prostaglandin inhibitors provide therapy for pain, fever and inflammation for example, in the treatment of rheumatoid arthritis and osteoarthritis. The non-steroidal antiinflammatory drugs (NSAIDs) such as ibuprofen, naproxen and fenamates inhibit both isozymes, prostaglandin endoperoxide H synthase 1 (PGHS-1) and prostaglandin endoperoxide H synthase 2 (PGHS-2). Inhibition of the constitutive enzyme PGHS-1 results in gastrointestinal side effects including ulcers and bleeding and incidence of renal problems with chronic therapy.

Inhibitors of the induced isozyme PGHS-2 are proposed to provide antiinflammatory activity without the side effects of PGHS-1 inhibitors. A general review of the current knowledge of PGHS-1 and PGHS-2 isozyme properties and a summary of inhibitors and their activity has been reviewed by: (1) Battistini, B.; Botting, R.; Bakhle, Y. S. "COX-1 and COX-2: Toward the Development of More Selective NSAIDs", Drug New and Perspectives, 1994, 7(8), 501–512; (2) DeWitt, D. L.; Bhattacharyya, D.; Lecomte, M.; Smith, W. L., "The Differential Susceptibility of Prostaglandin Endoperoxide H Synthases-1 and -2 to Nonsteroidal Anti-inflammatory Drugs: Aspirin Derivatives as Selective Inhibitors," Med. Chem. Res. 1995, 5(5), 325–343; (3) Mitchell, J. A.; Larkin, S.; Williams, T. J., "Cyclooxygenase-2: Regulation and Relevance in Inflammation," Biochem. Pharm., 1995, 50(10), 1535–1542.

Indomethacin and sulindac were developed as prostaglandin biosynthesis inhibitors prior to the discovery of the different isozyme forms. Both indomethacin and sulindac are reported to inhibit both PGHS-1 and PGHS-2 (Battistini, B.; Botting, R.; Bakhle, Y. S., op. cit.)

The current invention provides novel oxime containing derivatives of indole and indene compounds with unexpected preferential inhibitory activity against the induced PGHS-2 isozyme versus PGHS-1.

SUMMARY OF THE INVENTION

The present invention provides novel oxime derivatives of indole and indene compounds with unexpected preferrential inhibitory activity against the induced PGHS-2 isozyme versus PGHS-1.

In its principal embodiment, the present invention provides a compound of the formula

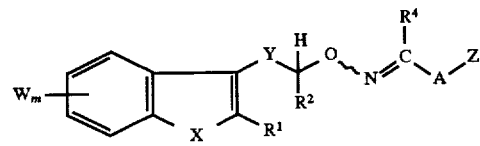

or a pharmaceutically acceptable salt thereof wherein m is an integer of one to three, inclusive.

W is independently selected at each occurrence from the group consisting of a) halogen; b) alkyl of one to six carbon atoms; c) haloalkyl of one to six carbon atoms; d) alkoxy of one to six carbon atoms; e) unsubstituted 2-thiazolylmethoxy; f) 2-thiazolylmethoxy substituted with one or two groups independently selected from halogen and haloalkyl of one to six carbon atoms; g) unsubstituted 2-benzothiazolylmethoxy; h) 2-benzothiazolylmethoxy substituted with one or two groups independently selected from halogen and haloalkyl of one to six carbon atoms; i) unsubstituted 2-pyridylmethoxy; j) 2-pyridylmethoxy substituted with one or two groups independently selected from halogen and haloalkyl of one to six carbon atoms; k) 2-quinolylmethoxy; and l) quinolylmethoxy substituted with one or two groups independently selected from halogen and haloalkyl of one to six carbon atoms; all of the foregoing with the proviso that when W is substituted or unsubstituted thiazolylmethoxy, benzothiazolylmethoxy, pyridylmethoxy, or quinolylmethoxy, m is limited to one.

X is selected from the group consisting of

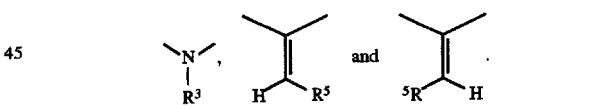

Y is absent or is alkylene of one to six carbon atoms; and A is absent or is selected from the group consisting of a) unsubstituted alkylene of one to six carbon atoms; b) alkylene of one to six carbon atoms substituted with one or two substituents independently selected from the group selected from —OH and alkoxy of one to six carbon atoms; c) unsubstituted alkenylene; d) alkenylene substituted with one or two alkoxy groups one to six carbon atoms; e) cycloalkylene of three to eight carbon atoms; f) cycloalkylene of three to eight carbon atoms substituted with one or two substituents independently selected from the group consisting of hydroxy and alkoxy of one to six carbon atoms; g) a phenylene ring substituted with one to three groups independently selected from the group consisting of hydroxy, alkoxy of one to six carbon atoms and alkyl of one to six carbon atoms; and h) alternatively, A and $R^4$, together with the carbon atom to which they are attached, form a tetrahydropyranyl or tetrahydrothiopyranyl ring with the Z group being optionally attached to the ring thus formed.

Z is selected from the group consisting of a) hydrogen; b) —C(O)M; c) hydroxy; d) alkoxy of one to six carbon atoms; e) unsubstituted phenoxy; f) phenoxy substituted with one or two substituents independently selected from alkyl of one to six carbon atoms and alkoxy of one to six carbon atoms; g) tetrazolyl; h) —CH=NOH; and i) —CH=NOR where R is alkyl of one to six carbon atoms and M is selected from the group consisting of hydroxy or a pharmaceutically acceptable cation thereof; alkoxy of one to six carbon atoms; and —NR$^7$R$^8$.

R$^1$ is selected from the group consisting of a) hydrogen, b) hydroxy, c) alkyl of one to six carbon atoms, and d) hydroxyalkyl of one to six carbon atoms.

R$^2$ is selected from the group consisting of a) hydrogen; b) alkyl of one to six carbon atoms; c) unsubstituted phenyl; d) phenyl substituted with one to three groups independently selected from the group consisting of halogen, alkyl of one to six carbon atoms, haloalkyl of one to six carbon atoms, and alkoxy of one to six carbon atoms; e) unsubstituted phenylalkyl in which the alkyl portion is of one to six carbon atoms; and f) phenylalkyl in which the alkyl portion is of one to six carbon atoms and the phenyl ring is substituted with one to three groups independently selected from the group consisting of halogen, alkyl of one to six carbon atoms, haloalkyl of one to six carbon atoms, and alkoxy of one to six carbon atoms.

R$^3$ is selected from the group consisting of a) unsubstituted benzoyl; b) benzoyl substituted with one or two substituents independently selected from the group consisting of halogen, alkyl of one to six carbon atoms, and alkoxy of one to six carbon atoms; c) unsubstituted benzyl; d) benzyl substituted with one or two substituents independently selected from the group consisting of halogen, alkyl of one to six carbon atoms, and alkoxy of one to six carbon atoms; e) unsubstituted pyridyl; f) pyridyl substituted with one or two substituents independently selected from the group consisting of halogen, alkyl of one to six carbon atoms, and alkoxy of one to six carbon atoms; g) alkoxycarbonyl of two to six carbon atoms; h) unsubstituted phenyl; i) phenyl substituted with one or two substituents independently selected from the group consisting of halogen, alkyl of one to six carbon atoms, alkoxy of one to six carbon atoms, —SR, and —S(O)R where R is alkyl of one to six carbon atoms; i) unsubstituted pyridyl; and j) pyridyl substituted with one or two substituents independently selected from the group consisting of halogen, alkyl of one to six carbon atoms, alkoxy of one to six carbon atoms.

R$^4$ is selected from the group consisting of a) hydrogen; b) alkyl of one to six carbon atoms; c) unsubstituted phenyl; d) phenyl substituted with one to three substituents independently selected from the group consisting of alkyl of one to six carbon atoms, and alkoxy of one to six carbon atoms; e) thienyl; and f) furanyl.

R$^5$ is selected from a) unsubstituted phenyl; b) phenyl substituted with one or two substituents independently selected from the group consisting of halogen, alkyl of one to six carbon atoms, alkoxy of one to six carbon atoms, —SR, and —S(O)R where R is alkyl of one to six carbon atoms; c) unsubstituted pyridyl; and d) pyridyl substituted with one or two substituents independently selected from the group consisting of halogen, alkyl of one to six carbon atoms, alkoxy of one to six carbon atoms.

R$^7$ and R$^8$ are independently selected from the group consisting of a) hydrogen, b) alkyl of one to six carbon atoms, c) hydroxyalkyl of one to six carbon atoms and d) hydroxy; with the proviso that R$^7$ and R$^8$ may not both be hydroxy.

In another embodiment, the present invention also provides pharmaceutical compositions useful for inhibiting prostaglandin biosynthesis comprising a therapeutically effective amount of compound of claim 1 in combination with a pharmaceutically acceptable carrier.

In yet another embodiment, the present invention provides a method of inhibiting prostaglandin biosynthesis in a host mammal in need of such treatment comprising administering to a mammal in need of such treatment a therapeutically effective amount of a compound of claim 1.

DETAILED DESCRIPTION

As used throughout this specification and the appended claims, the following terms have the meanings specified.

The term alkyl refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms alkoxy and alkoxyl denote an alkyl group, as defined above, attached to the parent molecular moiety through an oxygen atom. Representative alkoxy groups include methoxy, ethoxy, propoxy, butoxy, and the like.

The terms alkenyl as used herein refer to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term alkylene denotes a divalent group derived from a straight or branched chain saturated hydrocarbon containing by the removal of two hydrogen atoms, for example —CH$_2$—, —CH$_2$CH$_2$—, —CH(CH$_3$)CH$_2$— and the like.

The term alkenylene represents a divalent group derived from a straight or branched hydrocarbon group containing one single bond.

The term aryl as used herein refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

The term cycloalkyl as used herein refer to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

Cycloalkylene denotes a divalent radical derived from a cycloalkane by the removal of two hydrogen atoms.

The term haloalkyl denotes an alkyl group, as defined above, having one, two, or three halogen atoms attached thereto and is exemplified by such groups as chloromethyl, bromoethyl, trifluoromethyl, and the like.

By pharmaceutically acceptable salt it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art for example, S. M. Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

In one preferred embodiment, the present invention provides substituted indole compounds of the formula

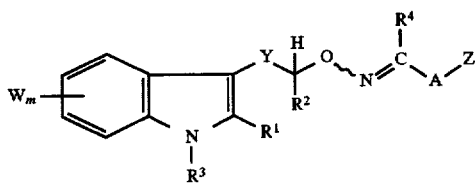

where A, W, Y, Z, m, $R^1$, $R^2$, $R^3$ and $R^4$, are as defined above.

Compounds falling within the scope of this embodiment of the invention include, but are not limited to:

glyoxylic acid-O-[2-(4-chlorobenzoyl-5-methoxy-2-methylindol-3-yl)ethyl] oxime 2-thienylglyoxylic acid-O-[2-(4-chlorobenzoyl-5-methoxy-2-methylindol-3-yl) ethyl] oxime;

2-phenylglyoxylic acid-O-[2-(4-chlorobenzoyl-5-methoxy-2-methylindol-3-yl)ethyl] oxime;

4-carboxyphenyl methyl ketone-O-[2-(4-chlorobenzoyl-5-methoxy-2-methylindol-3-yl)ethyl] oxime;

2-oxohexanoic acid-O-[2-(4-chlorobenzoyl-5-methoxy-2-methylindol-3-yl)ethyl]oxime;

4-oxopent-2-enoic acid-2-O-[2-(4-chlorobenzoyl-5-methoxy-2-methylindol-3-yl)ethyl] oxime;

glyceraldehyde-O-[2-(1-(4-chlorobenzoyl)-5-methoxy-2-methylindol-3-yl)ethyl] oxime;

(2,3,5,6-tetrahydropyran-4-one-O-[2-(4-chlorophenylmethyl-5-methoxy-2-methylindol-3-yl) ethyl]oxime;

(2,3,5,6-tetrahydrothiopyran-4-one-O-[2-(4-chlorophenylmethyl-5-methoxy-2-methylindol-3-yl) ethyl]oxime;

glyoxylic acid-O-[2-(4-chlorophenylmethyl-5-methoxy-2-methylindol-3-yl)ethyl]oxime;

3-oxopropionic acid-O-[2-(4-chlorophenylmethyl-5-methoxy-2-methylindol-3-yl)ethyl]oxime;

hydroxyacetaldehyde-O-[2-(4-chlorophenylmethyl-5-methoxy-2-methylindol-3-yl)ethyl]oxime;

3-hydroxpropanal-O-[2-(4-chlorophenylmethyl-5-methoxy-2-methylindol-3-yl)ethyl]oxime;

methoxyacetaldehyde-O-[2-(4-chlorophenylmethyl-5-methoxy-2-methylindol-3-yl)ethyl]oxime;

3-methoxypropanal-O-[2-(4-chlorophenylmethyl-5-methoxy-2-methylindol-3-yl)ethyl]oxime;

phenoxyacetaldehyde-O-[2-(4-chlorophenylmethyl-5-methoxy-2-methylindol-3-yl)ethyl]oxime;

3-phenoxypropanal-O-[2-(4-chlorophenylmethyl-5-methoxy-2-methylindol-3-yl)ethyl]oxime;

2,3-dimethoxypropanal-O-[2-(4-chlorophenylmethyl-5-methoxy-2-methylindol-3-yl)ethyl]oxime;

glyoxal-O-[2-(4-chlorophenylmethyl-5-methoxy-2-methylindol-3-yl)ethyl]oxime;

5-formyltetrazole-O-[2-(4-chlorophenylmethyl-5-methoxy-2-methylindol-3-yl)ethyl]oxime;

glyoxylic acid-O-2-[1-(t-butoxycarbonyl)-5-(thiazol-2-ylmethoxy)-2-methylindol-3-yl]ethyloxime;

glyoxylic acid-O-2-[1-(3-pyridylmethyl)-5-(thiazol-2-ylmethoxy)-2-methylindol-3-yl]ethyloxime;

glyoxylic acid-O-2-[1-(t-butoxycarbonyl)-5-(benzothiazol-2-ylmethoxy)-2-methylindol-3-yl]ethyloxime;

glyoxylic acid-O-2-[1-(3-pyridylmethyl)-5-(benzothiazol-2-ylmethoxy)-2-methylindol-3-yl]ethyloxime;

glyoxylic acid-O-2-[1-(t-butoxycarbonyl)-5-(quinol-2-ylmethoxy)-2-methylindol-3-yl]ethyloxime;

glyoxylic acid-O-2-[1-(3-pyridylmethyl)-5-(quinol-2-ylmethoxy)-2-methylindol-3-yl]ethyloxime;

glyoxylic acid-O-2-[1-(t-butoxycarbonyl)-5-(pyrid-2-ylmethoxy)-2-methylindol-3-yl]ethyloxime; and glyoxylic acid-O-2-[1-(3-pyridylmethyl)-5-(quinol-2-ylmethoxy)-2-methylindol-3-yl]ethyloxime.

In another preferred embodiment, the present invention provides substituted indene compounds of the formulae

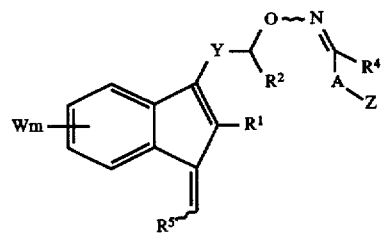

where A, W, Y, Z, m, $R^1$, $R^2$, $R^4$, and $R^5$, are as defined above.

Compounds falling within the scope of this embodiment of the invention include, but are not limited to:

glyoxylic acid-O-2-[Z-5-fluoro-2-methyl-1-(4-methylsulfinylphenyl)methylene-1H-inden-3-yl] ethyloxime;

3-oxopropionic acid-O-2-[Z-5-fluoro-2-methyl-1-(4-methylsulfinylphenyl)methylene-1H-inden-3-yl] ethyloxime;

2-oxopropionic acid-O-2-[Z-5-fluoro-2-methyl-1-(4-methylsulfinylphenyl)methylene-1H-inden-3-yl] ethyloxime;

hydroxyacetaldehyde-O-2-[Z-5-fluoro-2-methyl-1-(4-methylsulfinylphenyl)methylene-1H-inden-3-yl]ethyloxime;

3-hydroxypropanal-O-2-[Z-5-fluoro-2-methyl-1-(4-methylsulfinylphenyl)methylene-1H-inden-3-yl]ethyloxime;

methoxyacetaldehyde-O-2-[Z-5-fluoro-2-methyl-1-(4-methylsulfinylphenyl)methylene-1H-inden-3-yl]ethyloxime;

3-methoxypropanal-O-2-[Z-5-fluoro-2-methyl-1-(4-methylsulfinylphenyl)methylene-1H-inden-3-yl]ethyloxime;

phenoxyacetaldehyde-O-2-[Z-5-fluoro-2-methyl-1-(4-methylsulfinylphenyl)methylene-1H-inden-3-yl]ethyloxime;

phenoxypropanal-O-2-[Z-5-fluoro-2-methyl-1-(4-methylsulfinylphenyl)methylene-1H-inden-3-yl]ethyloxime;

glyceracetaldehyde-O-2-[Z-5-fluoro-2-methyl-1-(4-methylsulfinylphenyl)methylene-1H-inden-3-yl]ethyloxime;

2,3-dimethoxypropanal-O-2-[Z-5-fluoro-2-methyl-1-(4-methylsulfinylphenyl)methylene-1H-inden-3-yl]ethyloxime;

glyoxaloxime-O-2-[Z-5-fluoro-2-methyl-1-(4-methylsulfinylphenyl)methylene-1H-inden-3-yl]ethyloxime;

O-methylglyoxal-O-2-[Z-5-fluoro-2-methyl-1-(4-methylsulfinylphenyl)methylene-1H-inden-3-yl]ethyloxime;

5-formyltetrazole-O-2-[Z-5-fluoro-2-methyl-1-(4-methylsulfinylphenyl)methylene-1H-inden-3-yl]ethyloxime;

glyoxylic acid-O-2-[Z-5-fluoro-2-methyl-1-(4-methylthiophenyl)methylene-1H-inden-3-yl]ethyl oxime;

3-oxopropionic acid-O-2-[Z-5-fluoro-2-methyl-1-(4-methylthiophenyl)methylene-1H-inden-3-yl]ethyloxime;

2-oxopropionic acid-O-2-[Z-5-fluoro-2-methyl-1-(4-methylthiophenyl)methylene-1H-inden-3-yl]ethyloxime;

hydroxyacetaldehyde-O-2-[Z-5-fluoro-2-methyl-1-(4-methylthiophenyl)methylene-1H-inden-3-yl]ethyloxime;

3-hydroxypropanal-O-2-[Z-5-fluoro-2-methyl-1-(4-methylthiophenyl)methylene-1H-inden-3-yl]ethyloxime;

methoxyacetaldehyde-O-2-[Z-5-fluoro-2-methyl-1-(4-methylsulfinylphenyl)methylene-1H-inden-3-yl]ethyloxime;

3-methoxypropanal-O-2-[Z-5-fluoro-2-methyl-1-(4-methylthiophenyl)methylene-1H-inden-3-yl]ethyloxime;

phenoxyacetaldehyde-O-2-[Z-5-fluoro-2-methyl-1-(4-methylthiophenyl)methylene-1H-inden-3-yl]ethyloxime;

phenoxypropanal-O-2-[Z-5-fluoro-2-methyl-1-(4-methylthiophenyl)methylene-1H-inden-3-yl]ethyl oxime;

glyceracetaldehyde-O-2-[Z-5-fluoro-2-methyl-1-(4-methylthiophenyl)methylene-1H-inden-3-yl]ethyloxime;

2,3-dimethoxypropanal-O-2-[Z-5-fluoro-2-methyl-1-(4-methylthiophenyl)methylene-1H-inden-3-yl]ethyloxime;

glyoxal-O-2-[Z-5-fluoro-2-methyl-1-(4-methylthiophenyl)methylene-1H-inden-3-yl]ethyloxime;

O-methylglyoxal-O-2-[Z-5-fluoro-2-methyl-1-(4-methylthiophenyl)methylene-1H-inden-3-yl]ethyloxime;

5-formyltetrazole-O-2-[Z-5-fluoro-2-methyl-1-(4-methylthiophenyl)methylene-1H-inden-3-yl]ethyloxime;

glyoxylic acid-O-2-[Z-5-fluoro-2-methyl-1-(4-pyridyl)methylene-1H-inden-3-yl]ethyloxime;

3-oxopropionic acid-O-2-[Z-5-fluoro-2-methyl-1-(4-pyridyl)methylene-1H-inden-3-yl]ethyloxime;

2-oxopropionic acid-O-2-[Z-5-fluoro-2-methyl-1-(4-pyridyl)methylene-1H-inden-3-yl]ethyloxime;

hydroxyacetaldehyde-O-2-[Z-5-fluoro-2-methyl-1-(4-pyridyl)methylene-1H-inden-3-yl]ethyloxime;

3-hydroxypropanal-O-2-[Z-5-fluoro-2-methyl-1-(4-pyridyl)methylene-1H-inden-3-yl]ethyloxime;

methoxyacetaldehyde-O-2-[Z-5-fluoro-2-methyl-1-(4-pyridyl)methylene-1H-inden-3-yl]ethyloxime;

3-methoxypropanal-O-2-[Z-5-fluoro-2-methyl-1-(4-pyridyl)methylene-1H-inden-3-yl]ethyloxime;

phenoxyacetaldehyde-O-2-[Z-5-fluoro-2-methyl-1-(4-pyridyl)methylene-1H-inden-3-yl]ethyloxime;

phenoxypropanal-O-2-[Z-5-fluoro-2-methyl-1-(4-pyridyl)methylene-1H-inden-3-yl]ethyloxime;

glyceracetaldehyde-O-2-[Z-5-fluoro-2-methyl-1-(4-pyridyl)methylene-1H-inden-3-yl]ethyloxime;

2,3-dimethoxypropanal-O-2-[Z-5-fluoro-2-methyl-1-(4-pyridyl)methylene-1H-inden-3-yl]ethyloxime;

glyoxal-O-2-[Z-5-fluoro-2-methyl-1-(4-pyridyl)methylene-1H-inden-3-yl]ethyloxime;

O-methylglyoxal-O-2-[Z-5-fluoro-2-methyl-1-(4-pyridyl)methylene-1H-inden-3-yl]ethyloxime; and 5-formyltetrazole-O-2-[Z-5-fluoro-2-methyl-1-(4-pyridyl)methylene-1H-inden-3-yl]ethyloxime.

Particularly preferred compounds are those where $R^1$ is alkyl of one to six carbon atoms, most preferably methyl; Y is methylene; and $R^2$ is hydrogen.

Prostaglandin Inhibition Determination

Inhibition of prostaglandin biosynthesis was evaluated against:

1. recombinant human prostaglandin hydroperoxidase -1 (cyclooxygenase-1)
2. recombinant human prostaglandin hydroperoxidase -2 (cyclooxygenase-2)
3. IL-1$\beta$ induced PGE$_2$ production in human amnionic WISH cells.

The methods used are described as follows.

Recombinant Human PGHS-1 and PGHS-2 Enzyme Assays

Compound dissolved in DMSO (3.3% v/v) was preincubated with microsomes from recombinant human PGHS-1 or PGHS-2 expressed in the baculovirus/Sf9 cell system (Gierse, J. K., Hauser, S. D., Creely, D. P., Koboldt, C., Rangwala, S., H., Isakson, P. C., and Seibert, K. Expression and selective inhibition of the constituitive and inducible forms of cyclooxygenase Biochem J. 1995, 305: 479.), together with the cofactors phenol (2 mM) and hematin (1 $\mu$M) for 60 minutes prior to the addition of 10 $\mu$M arachidonic acid. The reaction was allowed to run for 2.5 minutes at room temperature prior to quenching with HCl and neutralization with NaOH. PGE$_2$ production in the presence and absence of the drug was determined by EIA analysis.

EIA Determination of Prostaglandins

EIA reagents for prostaglandin determination were purchased from Perseptive Diagnostics, Cambridge, Mass. PGE$_2$ levels in lavage fluids were determined after the samples were dried under nitrogen and reconstituted with assay buffer. PGE$_2$ levels in enzyme assays or cell culture media were measured against standards prepared in the same milieu. The immunoassays were conducted as recommended by the manufacturer. The EIA was conducted in 96 well microtiter plates (Nunc Roskilde, Denmark) and optical density measured using a microplate reader (Vmax, Molecular Devices Corp., Menlo Park, Calif.).

IL-1β Induced PGE$_2$ Production in WISH Cells

Human amnionic WISH (Albert, T. J., Su, H.-S., Zimmerman, P. D., Iams, J. D. and Kniss, D. A. Interleukin-1β regulates the inducible cyclooxygenase in amnion-derived WISH cells. *Prostaglandins*, 1994, 48:401) cells were grown to 80% confluence in 48 well plates. Following removal of the growth medium and two washings with Gey's Balanced Salt Solution, 5 ng IL-1β/ml (UBI, Lake Placid, N.Y.) was added to the cells with or without compound in DMSO (0.01% v/v) in Neuman-Tytell Serumless Medium (GIBCO, Grand Island, N.Y.). Following an 18 hour incubation to allow for the maximal induction of PGHS-2, the conditioned medium was removed and assayed for PGE$_2$ content by EIA.

The compounds of this invention inhibit prostaglandin biosynthesis as shown by the data for the representative Example 1 in Table 1.

TABLE 1

In Vitro Inhibitory Potencies Against Human Recombinant PGHS-1 and PGHS-2

| Example | PGHS-1 IC$_{50}$ (μM) | PGHS-2 IC$_{50}$ (μM) |
|---------|----------------------|----------------------|
| 6 | 52 | 0.07 |
| 7 | 24 | 0.06 |
| 8 | 0% @ 1.0 μM | 72% @ 0.1 μM |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The compounds of this invention can be prepared by representative methods described as follows. The synthetic chemistry developed in the study of indomethacin, sulindac and corresponding analogs provides a foundation of chemical art (Shen, T. Y. and Winter, C. A. Chemical and biological studies on indomethacin, sulindac and their analogs, in Advances in Drug Research, Vol. 12, Simmonds, A. B., Ed., Academic Press, New York, 1977, 89 and Gund, P.; Shen, T. Y. A model for the prostaglandin synthetase cyclooxygenase site and its inhibition by antiinflammatory arylacetic acids, J. Med. Chem. 20, 1146, 1977.) for the preparation of many of the compounds of this invention.

One general method for the preparation of indole containing compounds of this invention is shown below in Reaction Scheme 1 and involves the reduction of the carboxylate group of an analog of indomethacin, 1, to the corresponding hydroxy intermediate 2. Treatment of intermediate 2 with N-hydroxyphthalimide, diisopropylazodicarboxylate and triphenylphosphine provided the intermediate oxyphthalimide adduct which was treated with hydrazine hydrate to provide the corresponding hydroxylamine intermediate 3. Reaction of the hydroxylamine intermediate 3 with the requisite carbonyl compound O=A—Z (4) provides a general synthetic route to indole compounds of the present invention, 5a.

Scheme 1

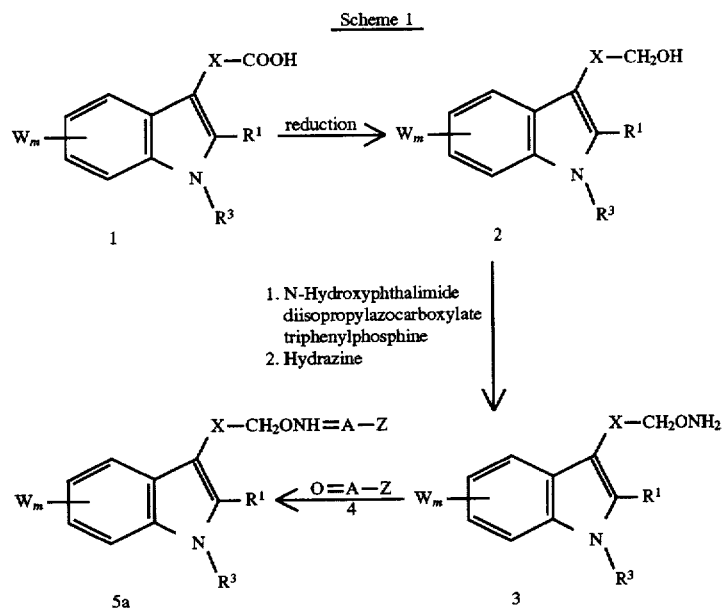

Compounds of the present invention where $R_2$ is other than hydrogen (5b) are prepared by the general synthetic sequence shown in Reaction Scheme 2 in which the aldehyde intermediate 6 (derived by standard methods of oxidation of intermediate 2 from Scheme 1) is reacted with an appropriate nucleophilic component of the radical $R^2$ such as a lithium carbanion form or Grignard reagent provides the hydroxy intermediate 7 which is converted to the corresponding hydroxylamine intermediate 8 which is subsequently reacted with the requisite carbonyl group 4.

A general method for the preparation of indane containing compounds of the present invention is shown in Reaction Scheme 3 and involves the selective reduction of the carboxylate group of an analog of sulindac, 9, to the corresponding hydroxy intermediate 10, followed by conversion to the corresponding hydroxylamine, 11, and reaction with the requisite carbonyl group 4 as described above in Scheme 1 to provide compounds of the present invention where the $R^2$ group adjacent to the oximino functional group is hydrogen (12a).

Scheme 2

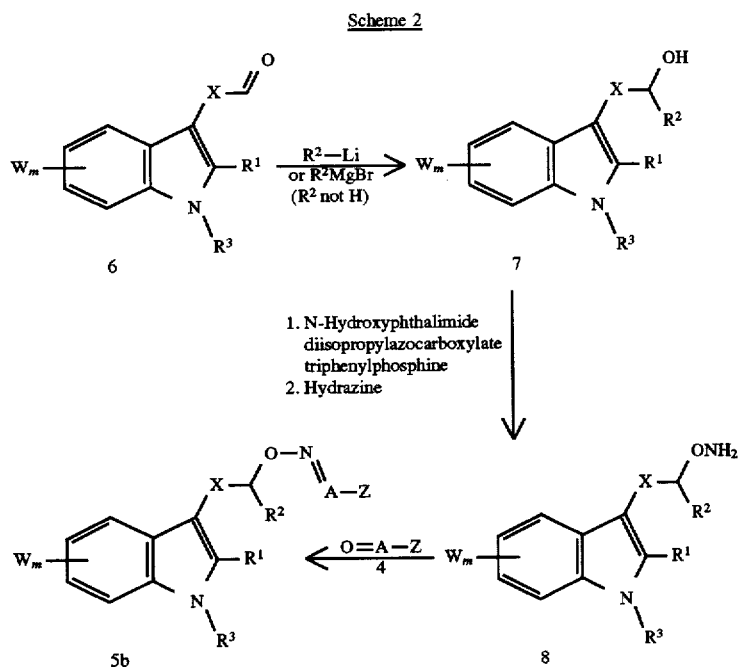

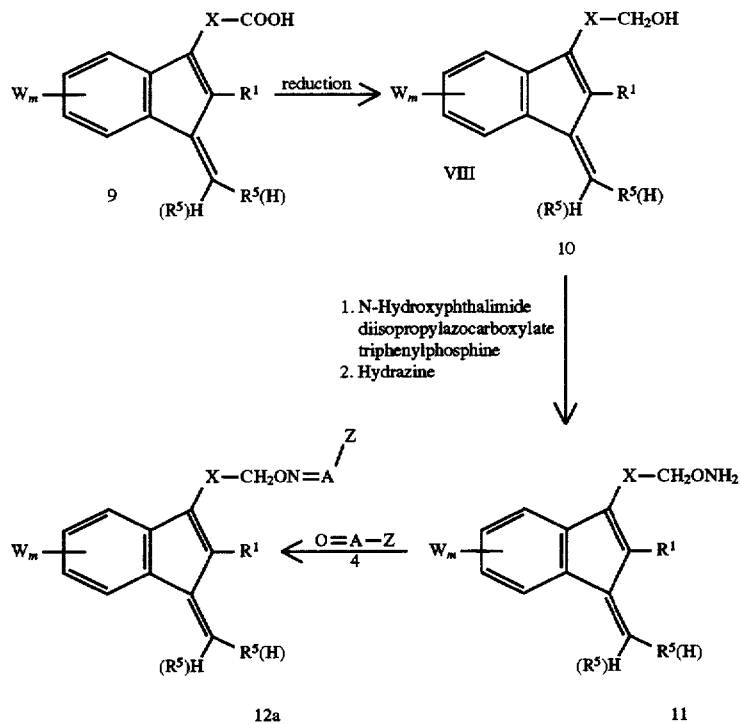

Indane compounds of the present invention where the $R^2$ group adjacent to the oximino group is other than hydrogen, 12b, are prepared by the general synthetic sequence shown in Reaction Scheme 4. The aldehyde 13 is reacted with an appropriate nucleophilic component of the radical $R^2$ such as a lithium carbanion form or Grignard reagent to provide the hydroxy intermediate, 14, which is subsequently converted into the corresponding hydroxylamine, 15, and reacted with the requisite carbonyl group 4 as described above in Reaction Scheme.

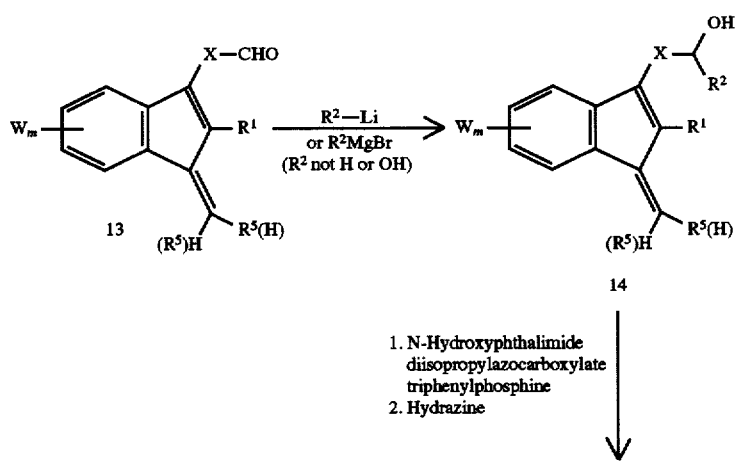

-continued
Scheme 4

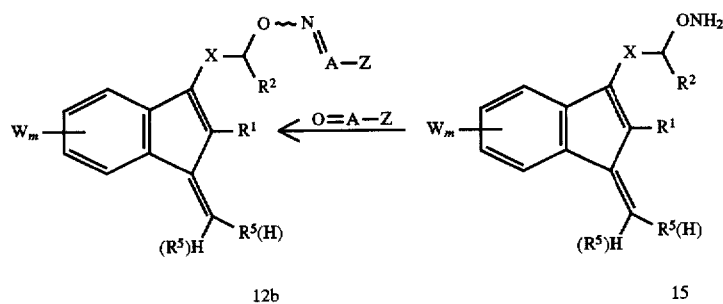

Compounds of the present invention with variations of the groups W, X, and $R^3$ (19) are prepared by the general synthetic sequence outlined in Scheme 5. Reaction of the requisite indanone intermediate, 16, with an appropriate nucleophilic component of the radical $R^3$ such as a lithium carbanion or Grignard reagent provides the intermediate 17. The intermediate 17 is treated under standard aldol reaction conditions with the requiste carbonyl acid X—COOH (for example glyoxalic acid) in the presence of Triton B under acid catalyzed isomeration and dehydration conditions to provide the corresponding indene acetic acid intermediate 18 which is converted to compounds of the present invention using one of the previously described schemes.

The carbonyl intermediates O=A—Z are prepared by standard methods from published or commercial starting materials.

The foregoing may be better understood by reference to the following examples which are provided for illustration and not intended to limit the scope of the inventive concept. The compounds of this invention consist of E and Z isomers of the oxime function and R and S enantiomers when there is an asymmetric carbon center. The individual or mixtures of isomers and/or enantiomers are considered as part of this invention.

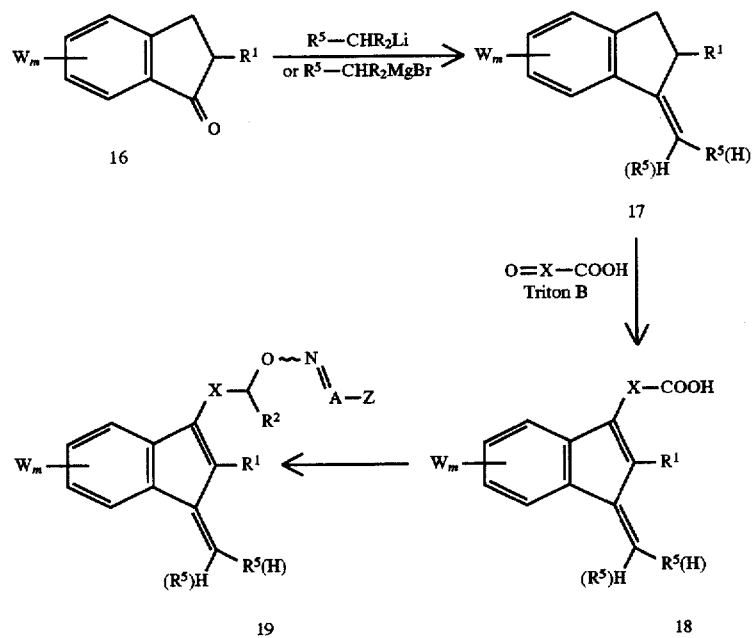

Scheme 5

EXAMPLE 1

Preparation of glyoxylic acid-O-[2-(4-chlorobenzoyl-5-methoxy-2-methylindol-3-yl)ethyl] oxime

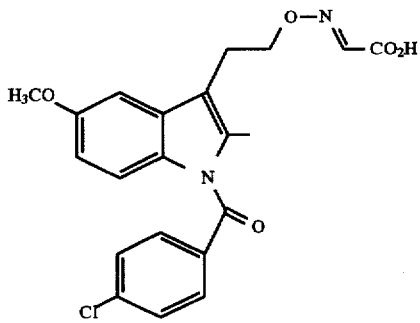

Step A: Preparation of 2-(4-chlorobenzoyl-5-methoxy-2-methylindol-3-yl)ethanol

To a magnetically stirred solution of indomethacin (7.5 g, 21 mmol) in dry THF (42 mL) was added dropwise $BH_3$:THF (1.0M in THF, 22 mL) at $-20°$ C., and the mixture was stirred at 0° C. for 2 hours. Crushed ice was added and the mixture was poured into 10% aqueous citric acid (200 mL) and extracted with ethyl acetate (3×100 mL). The combined organic layers were washed with water and brine, dried over $MgSO_4$, filtered, and evaporated in vacuo. Purification by chromatography (silica gel, 10:3 hexane/EtOAc) afforded 6.95 g (96.7%) of 2-(4-chlorobenzoyl-5-methoxy-2-methylindol-3-yl) ethanol.

Step B: Preparation of N-phthaloyl-O-2-[4-chlorobenzoyl-5-methoxy-2-methylindol-3-yl]ethyl hydroxylamine To a solution containing 2-(4-chlorobenzoyl-5-methoxy-2-methylindol-3-yl) ethanol (8.37 g, 24.4 mmol), triphenylphosphine (9.59 g, 36.6 mmol) and N-hydroxyphthalimide (5.97 g, 36.6 mmol) in THF (150 mL) at 0° C. was added diisopropyldiazodicarboxlate (5.97 mL, 36.6 mmol) and the solution was maintained cold for 16 hr after which it was evaporated in vacuo and chromatographed (silica gel, 4% ethyl acetate-methylene chloride) to provide the phthalimide intermediate as an off white solid (10.9 g, 91%).

Step C: Preparation of O-2-[4-chlorobenzoyl-5-methoxy-2-methylindol-3-yl]ethyl hydroxylamine To a solution containing the phthalimide intermediate (5.91 g, 12.1 mmol) in EtOH (35 mL) and methylene chloride (35 mL) at 0° C. was added hydrazine hydrate (0.8 mL, 25.4 mmol). The solution was allowed to come to ambient temperature and stirred for 3 hr, aqueous $NaHCO_3$ was added and the mixture was extracted with ethyl acetate (150 mL), washed with brine, dried with $MgSO_4$, and concentrated in vacuo to yield a tan solid (3.2 g, 74%). m.p. 83°–85° C. $^1H$ NMR (300 MHz) (DMSO-$d_6$) δ2.21 (s, 3H), 2.91 (m, 2H), 3.72 (m, 2H), 3.89 (s, 3H), 6.01 (s, 2H), 6.72 (dd, J=3.0, 9.0 Hz, 1H), 6.93 (d, J=9.0 Hz, 1H), 7.07 (d, J=3.0 Hz, 1H), 7.65 (m, 4H). MS (DCI/NH₃) m/z 359 (M+H)⁺. Anal. Calcd for $C_{19}H_{19}N_2O_3Cl$: C, 63.54; H, 5.33; N, 7.80. Found: C, 63.54; H, 5.24; N, 7.69.

Step D: Preparation of glyoxylic acid-O-[2-(4-chlorobenzoyl-5-methoxy-2-methylindol-3-yl)ethyl] oxime A solution of the hydroxylamine intermediate (0.7 g, 1.95 mmol) and glyoxylic acid (0.29 g, 2.15 mmol) in THF was stirred for 16 hr. The solution was then diluted with aqueous citric acid and extracted with ethyl acetate (100 mL). The extract was washed with brine, dried with $MgSO_4$, and concentrated in vacuo to yield an off white solid which was chromatographed (silica gel, 10% methanol-chloroform). The resulting residue was crystallized from ethyl ether-hexanes to provide the title compound as a white solid (0.35 g, 47%). m.p. 149°–153° C.; $^1H$ NMR (300 MHz) (DMSO-$d_6$) δ2.19 (s, 3H), 3.05 (m, 2H), 3.78 (s, 3H), 4.37 (m, 2H), 6.72 (dd, J=3.0, 9.0 Hz, 1H), 6.95 (d, J=9.0 Hz, 1H), 7.07 (d, J=3.0 Hz, 1H), 7.65 (m, 4H) 13.30 (s, 1H). MS (DCI/-NH₃) m/z 415 (M+H)⁺. Anal. Calcd for $C_{21}H_{19}N_2O_5Cl$: C, 60.80; H, 4.61; N, 6.75: Found: C, 61.10; H, 4.86; N, 6.45.

EXAMPLE 2

Preparation of 2-thienylglyoxylic acid-O-[2-(4-chlorobenzoyl-5-methoxy-2-methylindol-3-yl)ethyl] oxime

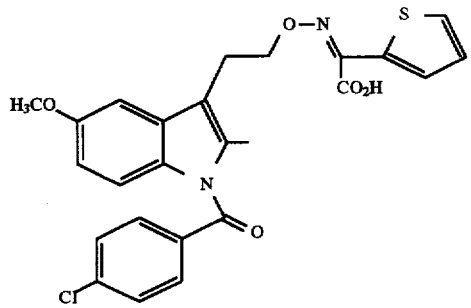

The title compound was prepared as described in Example 1 substituting 2-thienylglyoxylic acid for glyoxylic acid. m.p. 162°–164° C.; $^1H$ NMR (300 MHz) (DMSO-$d_6$) δ2.11 (s, 1.5H), 2.18 (s, 1.5H), 3.05 (m, 2H), 3.78 (s, 1.5H), 3.80 (s, 1.5H), 4.12 (m, 1H), 4.38 (m, 1.5H), 6.72 (m, 1H), 7.04 (m, 4H), 7.62 (m, 5H). MS (DCI/-NH₃) m/z 497 (M+H)⁺. Anal. Calcd for $C_{25}H_{21}N_2O_5SCl \times 1.0$ $H_2O$: C, 58.30; H, 4.50; N, 5.43: Found: C, 58.59; H, 4.00; N, 5.54.

EXAMPLE 3

Preparation of 2-phenylglyoxylic acid-O-[2-(4-chlorobenzoyl-5-methoxy-2-methylindol-3-yl)ethyl] oxime

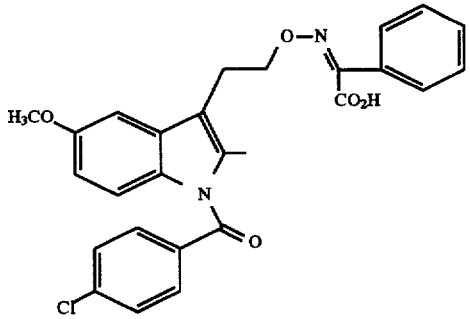

The title compound was prepared as described in Example 1 substituting 2-phenylglyoxylic acid (benzoylformic acid) for glyoxylic acid. m.p. 168°–173° C.; $^1H$ NMR (300 MHz) (DMSO-$d_6$) δ2.19 (s, 3H),3.02 (m, 2H), 3.80 (s, 3H), 4.17 (m, 2H), 6.72 (dd, J=3.0, 9.0 Hz, 1H), 7.09 (s, 2H), 7.34 (m, 3H), 7.61(m, 6H). MS (DCI/-NH₃) m/z 491 (M+H)⁺. Anal. Calcd for $C_{27}H_{23}N_2O_5Cl \times 1.0$ $H_2O$: C, 63.71; H, 4.95; N, 5.50. Found: C, 63.24; H, 4.45; N, 5.04.

EXAMPLE 4

Preparation of 4-carboxyphenyl methyl ketone-O-[2-(4-chlorobenzoyl-5-methoxy-2-methylindol-3-yl)ethyl] oxime

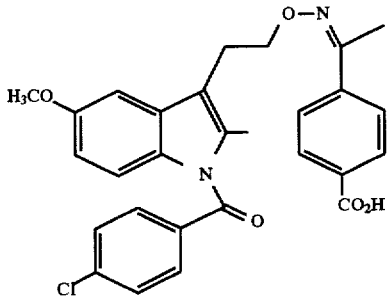

The title compound was prepared as described in Example 1 substituting 4-acetyl benzoic acid for glyoxylic acid. m.p. 176°–178° C.; $^1$H NMR (300 MHz) (DMSO-d$_6$) δ2.18 (s, 3H), 2.21 (s, 3H), 3.09 (m, 2H), 3.75 (s, 3H), 4.37 (m, 2H), 6.72 (dd, J=3.0, 9.0 Hz, 1H), 6.96 (d, J=7.5 Hz, 1H), 7.10 (d, J=3.0 Hz, 1H), 7.63 (s, 4H), 7.76 (d, J=9.0 Hz, 2H), 7.95 (s, J=9.0 Hz, 2H) 13.05 (s, 1H). MS (DCI/NH$_3$) m/z 505 (M+H)$^+$. Anal. Calcd for C$_{28}$H$_{25}$N$_2$O$_5$Cl: C, 66.59; H, 4.99; N,5.54. Found: C, 66.32; H, 4.83; N, 5.27.

EXAMPLE 5

Preparation of 2-oxohexanoic acid-O-[2-(4-chlorobenzoyl-5-methoxy-2-methylindol-3-yl)ethyl] oxime

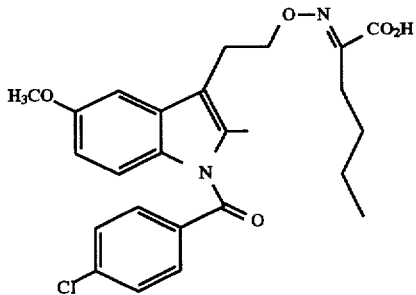

The title compound was prepared as described in Example 1 substituting 2-oxohexanoic acid for glyoxylic acid. m.p. 96°–99° C.; $^1$H NMR (300 MHz) (DMSO-d$_6$) δ0.78 (t, J=7.5 Hz, 3H), 1.20 (m, 4H), 2.20 (s, 3H), 2.28 (m, 2H), 3.04 (m, 2H), 3.79 (s, 3H), 4.38 (m, 2H), 6.70 (dd, J=3.0, 9.0 Hz, 1H), 6.93 (d, J=7.5 Hz, 1H), 7.08 (d, J=3.0 Hz, 1H), 7.63 (s, 4H), 12.95 (s, 1H). MS (DCI/NH$_3$) m/z 471 (M+H)$^+$. Anal. Calcd for C$_{25}$H$_{27}$N$_2$O$_5$Cl: C, 63.75; H, 5.77; N, 5.94. Found: C, 63.62; H, 5.71; N, 5.73.

EXAMPLE 6

Preparation of 4-oxopent-2-enoic acid-2-O-[2-(4-chlorobenzoyl-5-methoxy-2-methylindol-3-yl)ethyl] oxime

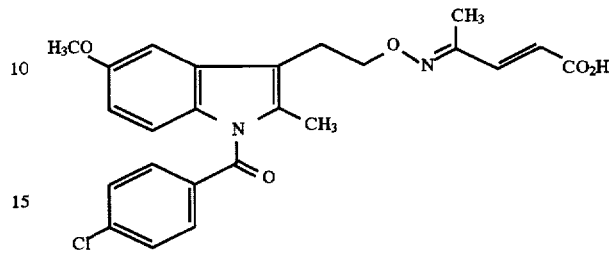

To a magnetically stirred solution of the hydroxylamine prepared in Example 1 (265 mg, 0.738 mmol) in a mixture of dry THF (5 mL) and ethanol (3 mL) was added 3-acetylacrylic acid (105 mg, 0.920 mmol). The solution was stirred overnight at ambient temperature and then concentrated in vacuo. The residue was dissolved in ethyl acetate (100 mL) and the solution was washed with satd aq NH$_4$Cl, dried (MgSO$_4$), filtered, and concentrated in vacuo to give a waxy solid. The product was chromatographed (silica gel, ethyl acetate-hexane 50:50, 60:40, 70:30) to afford 247 mg (0.543 mmol, 74%) of the title compound, which crystallized from EtOAc-hexane: mp 179°–181° C.; $^1$H NMR (300 MHz, DMSO-d$_6$) δ1.90 (s, 1.8H), 2.00 (s, 1.2H), 2.18 (s, 3H), 3.02 (m, 5H), 3.77 (s, 3H), 4.27 (t,J=6.4 Hz, 0.8H), 4.34 (t, J=6.4 Hz, 1.2H), 6.24 (d, J=16.2 Hz, 0.6H), 6.26 (d, J=16.2 Hz, 0.4H), 6.70 (dm, J=9.1 Hz, 1H), 6.94 (d, J=8.8 Hz, 1H), 7.04 (d, J=16.2 Hz, 0.6H), 7.06 (dm, J=2.4 Hz, 1H), 7.58 (d, J=16.2 Hz, 0.4H), 7.64 (m, 4H); MS (DCI/NH$_3$) m/z: 455 (M+1).

EXAMPLE 7

Preparation of glyceraldehyde-O-[2-(1-(4-chlorobenzoyl)-5-methoxy-2-methylindol-3-yl)ethyl] oxime

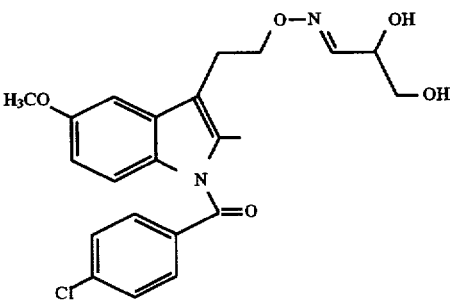

The title compound is prepared by reaction of O-2-[1-(4-chlorobenzoyl)-5-methoxy-2-methylindol-3-yl] ethylhydroxylamine with glyceraldehyde by the method of Example 1.

EXAMPLE 8

Preparation of (2,3,5,6-tetrahydropyran-4-one-O-[2-(4-chlorophenylmethyl-5-methoxy-2-methylindol-3-yl)ethyl] oxime

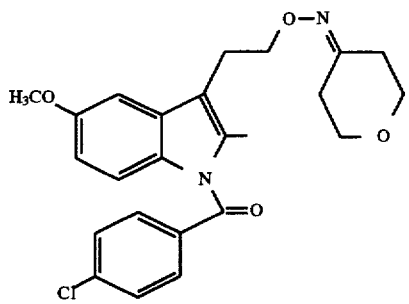

The title compound is prepared by reaction of O-2-[1-(4-chlorobenzoyl)-5-methoxy-2-methylindol-3-yl]ethylhydroxylamine with 2,3,5,6-tetrahydropyran-4-one by the method of Example 1.

EXAMPLE 9

Preparation of (2,3,5,6-tetrahydrothiopyran-4-one-O-[2-(4-chlorophenylmethyl-5-methoxy-2-methylindol-3-yl)ethyl] oxime

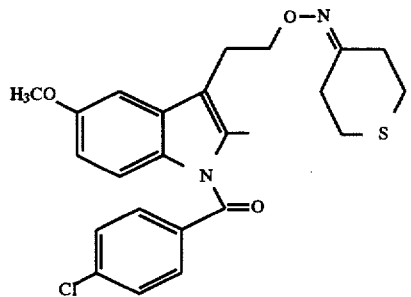

The title compound is prepared by reaction of O-2-[1-(4-chlorobenzoyl)-5-methoxy-2-methylindol-3-yl]ethylhydroxylamine with 2,3,5,6-tetrahydrothiopyran-4-one by the method of Example 1.

EXAMPLE 10

Preparation of O-2-[1-(4-chlorophenylmethyl)-5-methoxy-2-methylindol-3-yl]ethylhydroxylamine

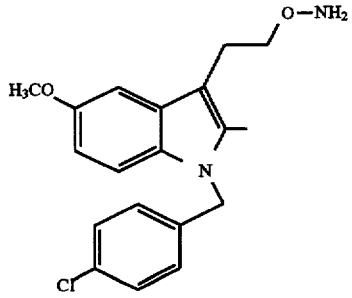

Step A: Preparation of 1-(4-chlorophenylmethyl)-5-methoxy-2-methyl-3-indoleacetic acid 4-chlorophenylmethyl ester To a solution of 5-methoxy-2-methyl-3-indoleacetic acid (4 g, 18.3 mmol) in anhydrous DMF (20 mL) at 0°–5° C. was added NaH (1.6 g, 60% dispersion in oil, 40 mmol) and stirred at room temperature for 40 min., then cooled again to 0°–5° C., and treated with 4-chlorophenylmethyl chloride (5.9 g, 36.6 mmol) and let stand at room temperature overnight. Water (50 ml) was added and the mixture was extracted with ethylacetate (100 mL), washed with brine and dried (MgSO$_4$), evaporated in vacuo, and purified by chromatography (silica gel, 10% ethylacetate in pentane) to yield 1-(4-chlorophenylmethyl)-5-methoxy-2-methyl-3-indoleacetic acid 4-chlorophenylmethyl ester.

Step B: Preparation of 2-[1-(4-chlorophenylmethyl)-5-methoxy-2-methylindol-3-yl]ethanol The ester intermediate (5.5 g, 11.8 mmol) was suspended in anhydrous ether (50 mL) and treated with LiAlH$_4$ (912 mg, 24 mmol) in ether (100 mL) at room temperature for 2 h. The reaction mixture was quenched sequentially with water (1 mL), 15% NaOH (1 mL) and water (3 mL). The precipitate was filtered and the filtrate was evaporated and purified by chromatography (silica gel, 30% EtOAC in pentane) to provide 4 g of 2-[1-(4-chlorophenylmethyl)-5-methoxy-2-methylindol-3-yl]ethanol.

Step C: Preparation of O-2-[1-(4-chlorophenylmethyl)-5-methoxy-2-methylindol-3-yl]ethylhydroxylamine A solution of 2-[1-(4-chlorophenylmethyl)-5-methoxy-2-methylindol-3-yl]ethanol (1 g, 3 mmol) in THF (10 mL) was treated with N-hydroxyphthalimide (489 mg, 3 mmol), triphenylphosphine (786 mg, 3 mmol) and diisopropylazodicarboxylate (606 mg, 3 mmol) at room temperature for 20 min. The mixture was concentrated in vacuo and chromatographed (silica gel, 1% ethylacetate in 1:1 pentane and dichloromethane) to provide 600 mg of the corresponding hydroxyphthalimide adduct.

A solution of the hydroxypthalimide adduct (400 mg, 0.84 mmol) in dichloromethane (5 mL) was treated with hydrazine hydrate (68 mg, 1.68 mmol) at room temperature. The mixture was stirred for 30 min, concentrated in vacuo, and purified by chromatography (silica gel, 2:1, pentane: dichloromethane) to provide 250 mg of O-2-[1-(4-chlorophenylmethyl)-5-methoxy-2-methylindol-3-yl]ethylhydroxylamine. mp. 92°–94° C.; NMR (DMSOd$_6$) δ2.31 (s, 3H), 2.88 (t, J=9 Hz, 2H), 3.64 (t, J=9 Hz, 2H), 3.76 (s, 3H), 5.34 (s, 2H), 5.90 (brs, 2H), 6.5 (dd, J=9 Hz, 3 Hz, 1H) 6.9 (dt, J=9 Hz, 1Hz, 2H), 6.97 (d, J=3 Hz, 1H), 7.21 (d, J=9 Hz, 1H), 7.33 (dt, J=9 Hz, 3 Hz, 2H). Mass Spec: (M$^+$) 345. Anal. Calc'd. for C$_{19}$H$_{21}$ClN$_2$O$_2$; C, 66.18; H, 6.14; N, 8.12. Found: C, 65.98; H, 6.04; N, 8.04.

EXAMPLE 11

Preparation of glyoxylic acid-O-[2-(4-chlorophenylmethyl-5-methoxy-2-methylindol-3-yl)ethyl] oxime

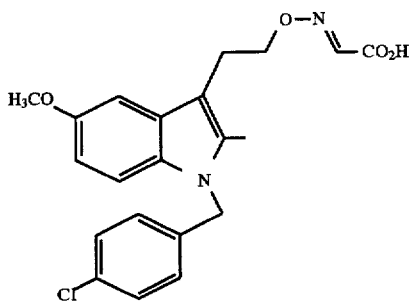

The title compound is prepared by reaction of O-2-[1-(4-chlorophenylmethyl)-5-methoxy-2-methylindol-3-yl]ethylhydroxylamine with glyoxylic acid by the method of Example 1.

EXAMPLE 12

Preparation of 3-oxopropionic acid-O-[2-(4-chlorophenylmethyl-5-methoxy-2-methylindol-3-yl)ethyl] oxime

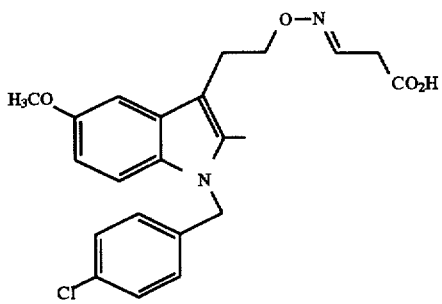

The title compound is prepared by reaction of O-2-[1-(4-chlorophenylmethyl)-5-methoxy-2-methylindol-3-yl]ethylhydroxylamine with 3-oxopropionic acid by the method of Example 1.

EXAMPLE 13

Preparation of hydroxyacetaldehyde-O-[2-(4-chlorophenylmethyl-5-methoxy-2-methylindol-3-yl)ethyl] oxime

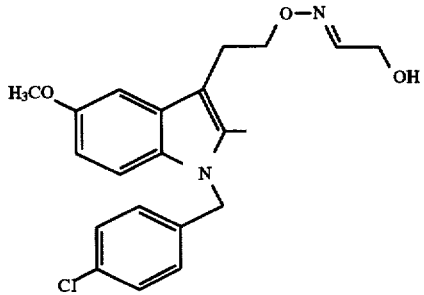

The title compound is prepared by reaction of O-2-[1-(4-chlorophenylmethyl)-5-methoxy-2-methylindol-3-yl]ethylhydroxylamine with hydroxyacetaldehyde by the method of Example 1.

EXAMPLE 14

Preparation of 3-hydroxpropanal-O-[2-(4-chlorophenylmethyl-5-methoxy-2-methylindol-3-yl)ethyl] oxime

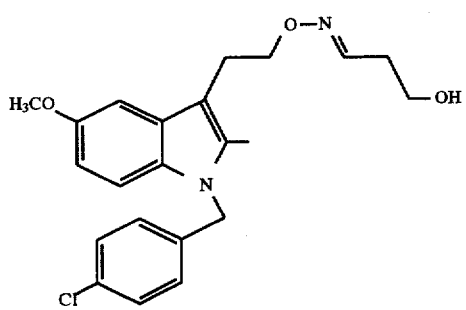

The title compound is prepared by reaction of O-2-[1-(4-chlorophenylmethyl)-5-methoxy-2-methylindol-3-yl]ethylhydroxylamine with 3-hydroxypropanal by the method of Example 1.

EXAMPLE 15

Preparation of methoxyacetaldehyde-O-[2-(4-chlorophenylmethyl-5-methoxy-2-methylindol-3-yl)ethyl] oxime

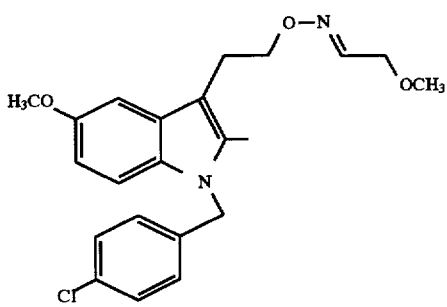

The title compound is prepared by reaction of O-2-[1-(4-chlorophenylmethyl)-5-methoxy-2-methylindol-3-yl]ethylhydroxylamine with methoxyacetaldehyde by the method of Example 1.

EXAMPLE 16

Preparation of 3-methoxypropanal-O-[2-(4-chlorophenylmethyl-5-methoxy-2-methylindol-3-yl)ethyl] oxime

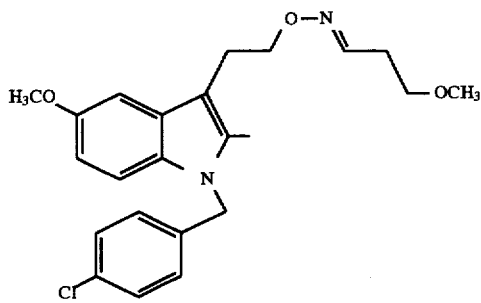

The title compound is prepared by reaction of O-2-[1-(4-chlorophenylmethyl)-5-methoxy-2-methylindol-3-yl]ethylhydroxylamine with 3-methoxypropanal by the method of Example 1.

EXAMPLE 17

Preparation of phenoxyacetaldehyde-O-[2-(4-chlorophenylmethyl-5-methoxy-2-methylindol-3-yl)ethyl] oxime

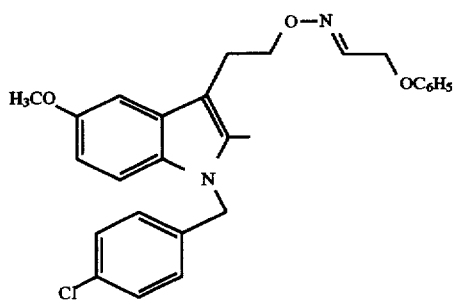

The title compound is prepared by reaction of O-2-[1-(4-chlorophenylmethyl)-5-methoxy-2-methylindol-3-yl]ethylhydroxylamine with phenoxyacetaldehyde by the method of Example 1.

EXAMPLE 18

Preparation of 3-phenoxypropanal-O-[2-(4-chlorophenylmethyl-5-methoxy-2-methylindol-3-yl)ethyl] oxime

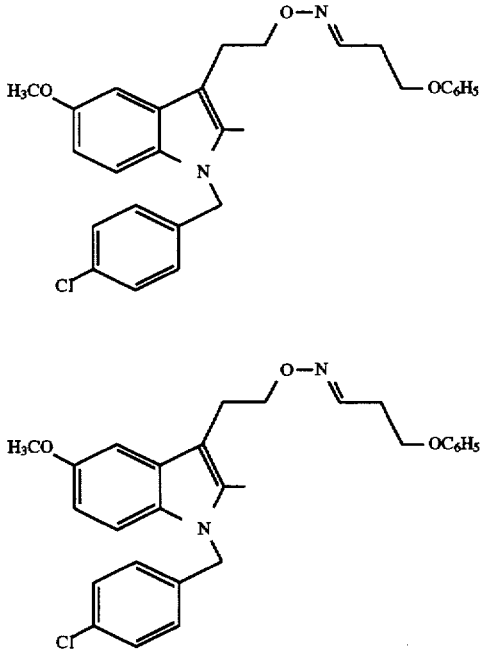

The title compound is prepared by reaction of O-2-[1-(4-chlorophenylmethyl)-5-methoxy-2-methylindol-3-yl]ethylhydroxylamine with 3-phenoxypropanal by the method of Example 1.

EXAMPLE 19

Preparation of 2,3-dimethoxypropanal-O-[2-(4-chlorophenylmethyl-5-methoxy-2-methylindol-3-yl)ethyl] oxime

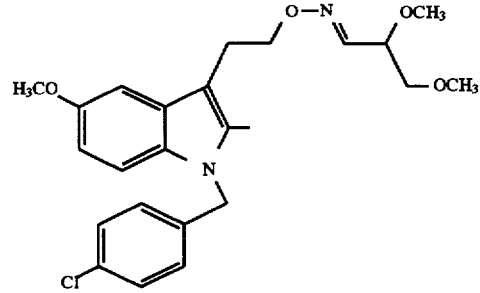

The title compound is prepared by reaction of O-2-[1-(4-chlorophenylmethyl)-5-methoxy-2-methylindol-3-yl]ethylhydroxylamine with 2,3-dimethoxypropanal by the method of Example 1.

EXAMPLE 20

Preparation of glyoxal-O-[2-(4-chlorophenylmethyl-5-methoxy-2-methylindol-3-yl)ethyl] oxime

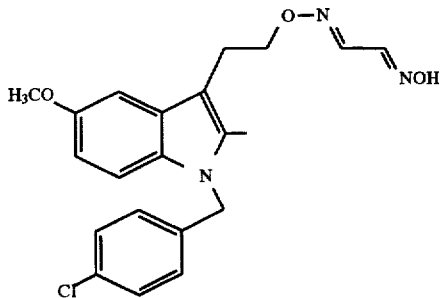

The title compound is prepared by reaction of O-2-[1-(4-chlorophenylmethyl)-5-methoxy-2-methylindol-3-yl]ethylhydroxylamine with glyoxaloxime by the method of Example 1.

EXAMPLE 21

Preparation of 5-formyltetrazole-O-[2-(4-chlorophenylmethyl-5-methoxy-2-methylindol-3-yl)ethyl] oxime

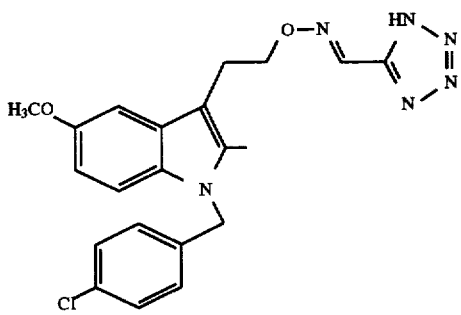

The title compound is prepared by reaction of O-2-[1-(4-chlorophenylmethyl)-5-methoxy-2-methylindol-3-yl]ethylhydroxylamine with 5-formyltetrazole by the method of Example 1.

EXAMPLE 22

Preparation of O-2-[1-(3-pyridylmethyl)-5-methoxy-2-methylindol-3-yl]ethylhydroxylamine

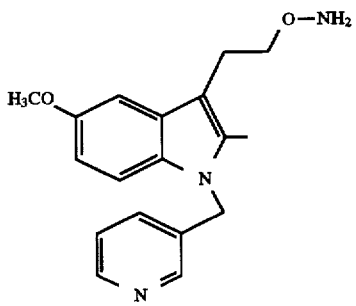

The title compound was prepared by the method of Example 7 substituting 3-pyridylmethyl chloride for 4-chlorophenylmethyl chloride.

EXAMPLE 23

Preparation of O-2-[1-(2-pyridylmethyl)-5-methoxy-2-methylindol-3-yl]ethylhydroxylamine

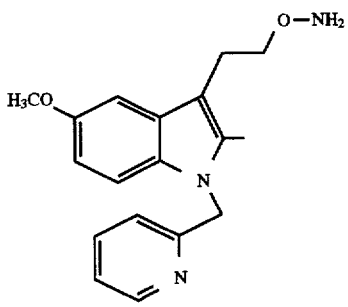

The title compound was prepared by the method of Example 7 substituting 2-pyridylmethyl chloride for 4-chlorophenylmethyl chloride.

EXAMPLE 24

Preparation of O-2-[1-(4-pyridylmethyl)-5-methoxy-2-methylindol-3-yl]ethylhydroxylamine

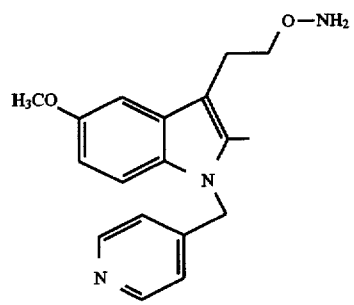

The title compound was prepared by the method of Example 7 substituting 4-pyridylmethyl chloride for 4-chlorophenylmethyl chloride.

EXAMPLE 25

Preparation of 1-(t-butoxycarbonyl)-5-hydroxy-2-methylindole acetic acid

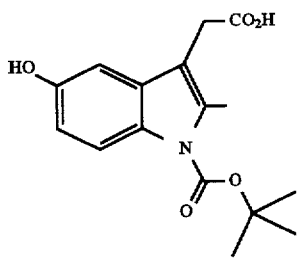

The title compound is prepared by standard N-tBOC formation on 5-methoxy-2-methyl-3-indoleacetic acid to provide 1-(t-butoxycarbonyl)-5-methoxy-2-methyl-3-indole acetic acid which is then demethylated by known methods such as $BBr_3$ or ethylthiol: $AlCl_3$.

EXAMPLE 26

Preparation of 2-[1-(t-butoxycarbonyl)-5-(thiazol-2-ylmethoxy)-2-methylindol-3-yl] ethanol

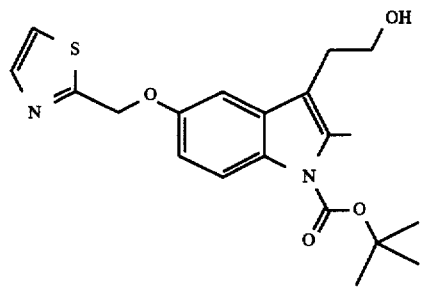

The title compound is prepared by reaction of two equivalents of thiazol-2-ylmethylchloride in the presence of a suitable base such as $K_2CO_3$ or NaH with 1-(t-butoxycarbonyl)-5-hydroxy-2-methylindole acetic acid to provide the dialkylated ester intermediate, 1-(t-butoxycarbonyl)-5-(thiazol-2-ylmethoxy)-2-methyl-3-indoleacetic acid thiazol-2-ylmethoxy ester which is subsequently saponified and the corresponding carboxylic acid is reduced with $BH_3$:THF to provide 2-[1-(t-butoxycarbonyl)-5-(thiazol-2-ylmethoxy)-2-methyl-3-indole] ethanol

EXAMPLE 27

Preparation of O-2-[1-(t-butoxycarbonyl)-5-(thiazol-2-ylmethoxy)-2-methylindol-3-yl] ethylhydroxylamine

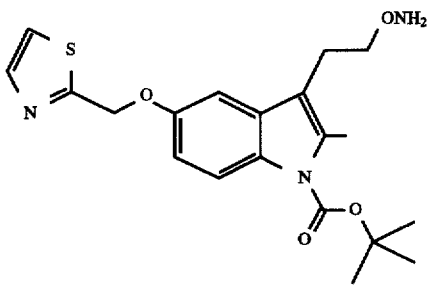

The title compound is prepared by conversion of 2-[1-(t-butoxycarbonyl)-5-(thiazol-2-ylmethoxy)-2-methyl-3-indole] ethanol to the corresponding hydroxylamine by the method described in Example 1.

EXAMPLE 28

Preparation of glyoxylic acid-O-2-[1-(t-butoxycarbonyl)-5-(thiazol-2-ylmethoxy)-2-methylindol-3-yl]ethyl oxime

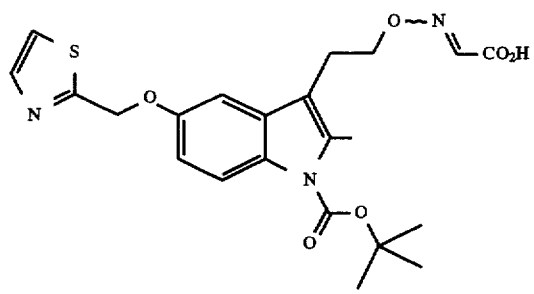

The title compound is prepared by reaction of O-2-[1-(t-butoxycarbonyl)-5-(thiazol-2-ylmethoxy)-2-methyl-3-indole]ethyl hydroxylamine with glyoxylic acid by the method described in Example 1.

EXAMPLE 29

Preparation of glyoxylic acid-O-2-[1-(3-pyridylmethyl)-5-(thiazol-2-ylmethoxy)-2-methylindol-3-yl]ethyl oxime

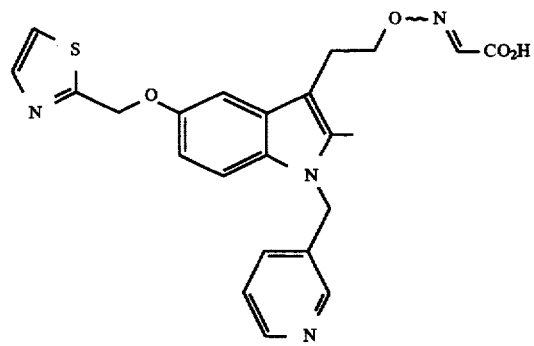

The title compound is prepared by reaction of glyoxylic acid-O-2-[1-(3-pyridylmethyl)-5-(thiazol-2-ylmethoxy)-2-methylindol-3-yl]ethyl oxime with trifluoroacetic acid to remove the t-BOC group followed by reaction of the indole intermediate with two equivalents of 3-pyridylmethyl chloride in the presence of a suitable base such as NaH to provide the intermediate glyoxylic acid 3-pyridyl ester-O-2-[1-(3-pyridylmethyl)-5-(thiazol-2-ylmethoxy)-2-methylindol-3-yl]ethyl oxime which is subsequently saponified.

EXAMPLE 30

Preparation of 2-[1-(t-butoxycarbonyl)-5-(benzothiazol-2-ylmethoxy)-2-methylindol-3-yl]ethanol

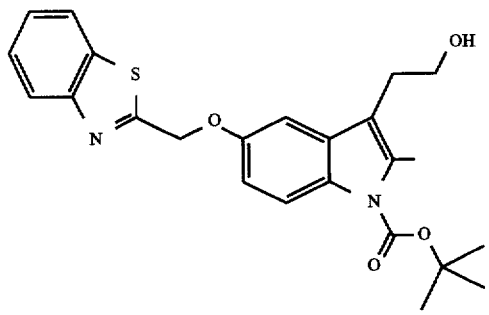

The title compound is prepared by reaction of two equivalents of benzothiazol-2-ylmethylchloride in the presence of a suitable base such as $K_2CO_3$ or NaH with 1-(t-butoxycarbonyl)-5-hydroxy-2-methylindole acetic acid to provide the dialkylated ester intermediate, 1-(t-butoxycarbonyl)-5-(benzothiazol-2-ylmethoxy)-2-methyl-3-indoleacetic acid benzothiazol-2-ylmethoxy ester which is subsequently saponified and the corresponding carboxylic acid is reduced with $BH_3$:THF to provide 2-[1-(t-butoxycarbonyl)-5-(benzothiazol-2-ylmethoxy)-2-methyl-3-indole] ethanol

EXAMPLE 31

Preparation of O-2-[1-(t-butoxycarbonyl)-5-(benzothiazol-2-ylmethoxy)-2-methylindol-3-yl] ethylhydroxylamine

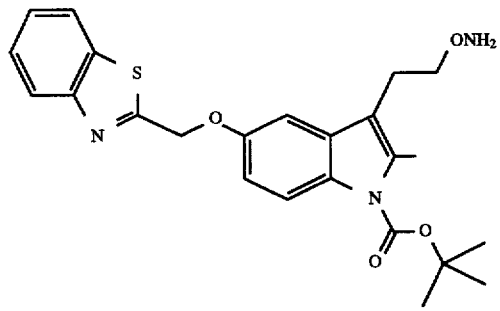

The title compound is prepared by conversion of 2-[1-(t-butoxycarbonyl)-5-(benzothiazol-2-ylmethoxy)-2-methyl-3-indole] ethanol to the corresponding hydroxylamine by the method described in Example 1.

EXAMPLE 32

Preparation of glyoxylic acid-O-2-[1-(t-butoxycarbonyl)-5-(benzothiazol-2-ylmethoxy)-2-methylindol-3-yl]ethyl oxime

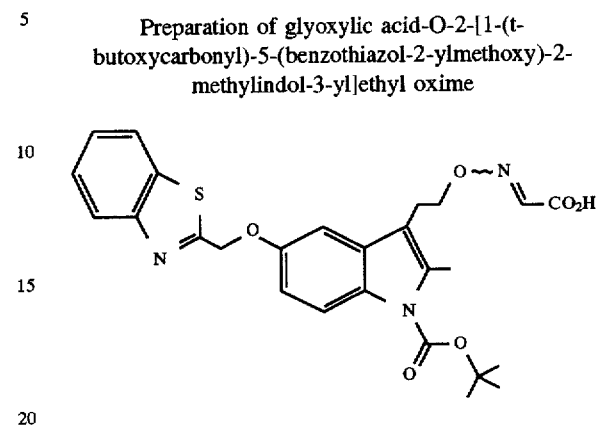

The title compound is prepared by reaction of O-2-[1-(t-butoxycarbonyl)-5-(benzothiazol-2-ylmethoxy)-2-methyl-3-indole]ethyl hydroxylamine with glyoxylic acid by the method described in Example 1.

EXAMPLE 33

Preparation of glyoxylic acid-O-2-[1-(3-pyridylmethyl)-5-(benzothiazol-2-ylmethoxy)-2-methylindol-3-yl]ethyl oxime

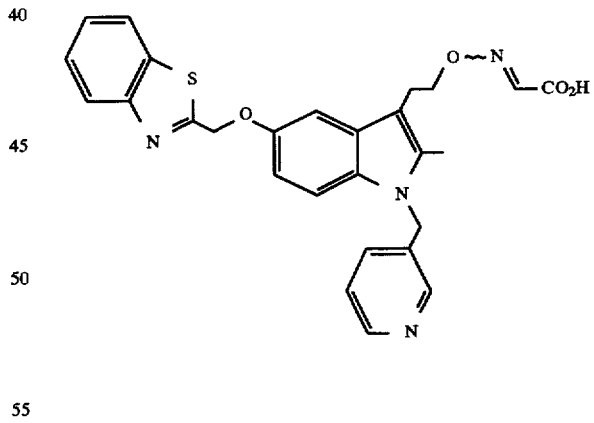

The title compound is prepared by reaction of glyoxylic acid-O-2-[1-(3-pyridylmethyl)-5-(benzothiazol-2-ylmethoxy)-2-methylindol-3-yl]ethyl oxime with trifluoroacetic acid to remove the t-BOC group followed by reaction of the indole intermediate with two equivalents of 3-pyridylmethyl chloride in the presence of a suitable base such as NaH to provide the intermediate glyoxylic acid 3-pyridyl ester-O-2-[1-(3-pyridylmethyl)-5-(benzothiazol-2-ylmethoxy)-2-methylindol-3-yl]ethyl oxime which is subsequently saponified.

EXAMPLE 34

Preparation of 2-[1-(t-butoxycarbonyl)-5-(quinol-2-ylmethoxy)-2-methylindol-3-yl] ethanol

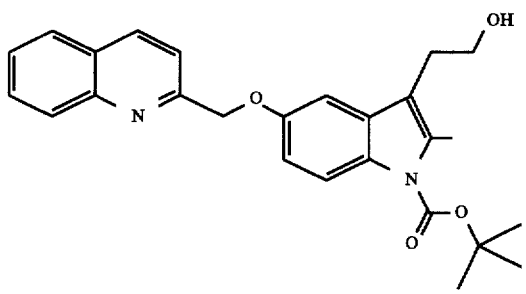

The title compound is prepared by reaction of two equivalents of quinol-2-ylmethylchloride in the presence of a suitable base such as $K_2CO_3$ or NaH with 1-(t-butoxycarbonyl)-5-hydroxy-2-methylindole acetic acid to provide the dialkylated ester intermediate, 1-(t-butoxycarbonyl)-5-(quinol-2-ylmethoxy)-2-methyl-3-indoleacetic acid quinol-2-ylmethoxy ester which is subsequently saponified and the corresponding carboxylic acid is reduced with $BH_3$:THF to provide 2-[1-(t-butoxycarbonyl)-5-(quinol-2-ylmethoxy)-2-methyl-3-indole] ethanol

EXAMPLE 35

Preparation of O-(1-(t-Butoxycarbonyl)-2-methyl-5-(2-quinolylmethoxy)indol-2-yl)ethylhydroxylamine

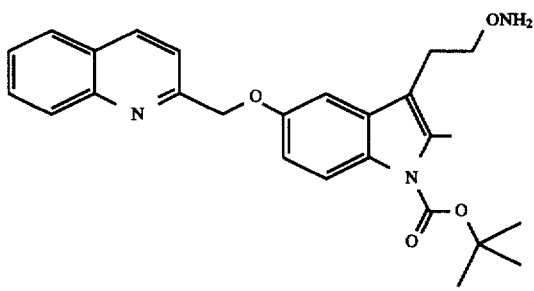

The title compound is prepared by conversion of 2-[1-(t-butoxycarbonyl)-5-(quinol-2-ylmethoxy)-2-methyl-3-indole] ethanol to the corresponding hydroxylamine by the method described in Example 1.

EXAMPLE 36

Preparation of glyoxylic acid-O-2-[1-(t-butoxycarbonyl)-5-(quinol-2-ylmethoxy)-2-methylindol-3-yl]ethyl oxime

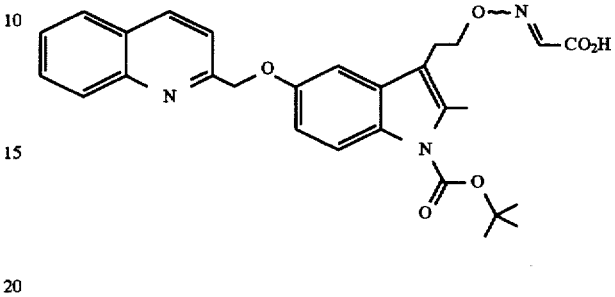

The title compound is prepared by reaction of O-2-[1-(t-butoxycarbonyl)-5-(quinol-2-ylmethoxy)-2-methyl-3-indole]ethyl hydroxylamine with glyoxylic acid by the method described in Example 1.

EXAMPLE 37

Preparation of glyoxylic acid-O-2-[1-(3-pyridylmethyl)-5-(quinol-2-ylmethoxy)-2-methylindol-3-yl]ethyl oxime

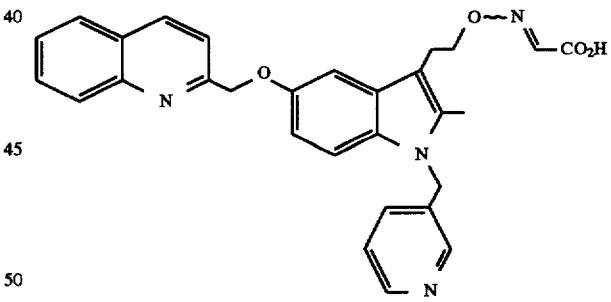

The title compound is prepared by reaction of glyoxylic acid-O-2-[1-(3-pyridylmethyl)-5-(quinol-2-ylmethoxy)-2-methylindol-3-yl]ethyl oxime with trifluoroacetic acid to remove the t-BOC group followed by reaction of the indole intermediate with two equivalents of 3-pyridylmethyl chloride in the presence of a suitable base such as NaH to provide the intermediate glyoxylic acid 3-pyridyl ester-O-2-[1-(3-pyridylmethyl)-5-(quinol-2-ylmethoxy)-2-methylindol-3-yl]ethyl oxime which is subsequently saponified.

EXAMPLE 38

Preparation of 2-[1-(t-butoxycarbonyl)-5-(pyrid-2-ylmethoxy)-2-methylindol-3-yl] ethanol

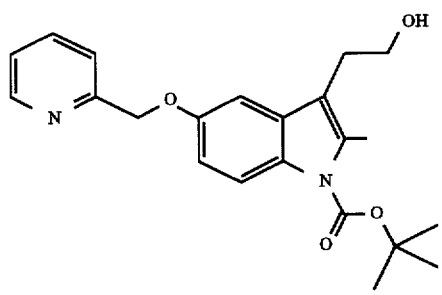

The title compound is prepared by reaction of two equivalents of pyrid-2-ylmethylchloride in the presence of a suitable base such as K₂CO₃ or NaH with 1-(t-butoxycarbonyl)-5-hydroxy-2-methylindole acetic acid to provide the dialkylated ester intermediate, 1-(t-butoxycarbonyl)-5-(pyrid-2-ylmethoxy)-2-methyl-3-indoleacetic acid pyrid-2-ylmethoxy ester which is subsequently saponified and the corresponding carboxylic acid is reduced with BH₃:THF to provide 2-[1-(t-butoxycarbonyl)-5-(pyrid-2-ylmethoxy)-2-methyl-3-indole] ethanol

EXAMPLE 39

Preparation of O-2-[1-(t-butoxycarbonyl)-5-(pyrid-2-ylmethoxy)-2-methylindol-3-yl] ethylhydroxylamine

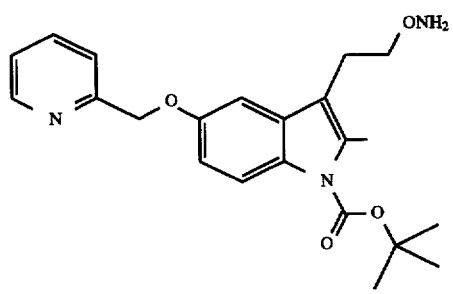

The title compound is prepared by conversion of 2-[1-(t-butoxycarbonyl)-5-(pyrid-2-ylmethoxy)-2-methyl-3-indole] ethanol to the corresponding hydroxylamine by the method described in Example 1.

EXAMPLE 40

Preparation of glyoxylic acid-O-2-[1-(t-butoxycarbonyl)-5-(pyrid-2-ylmethoxy)-2-methylindol-3-yl]ethyl oxime

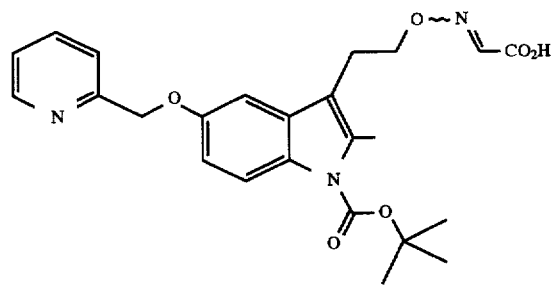

The title compound is prepared by reaction of O-2-[1-(t-butoxycarbonyl)-5-(pyrid-2-ylmethoxy)-2-methyl-3-indole] ethyl hydroxylamine with glyoxylic acid by the method described in Example 1.

EXAMPLE 41

Preparation of glyoxylic acid-O-2-[1-(3-pyridylmethyl)-5-(quinol-2-ylmethoxy)-2-methylindol-3-yl]ethyl oxime

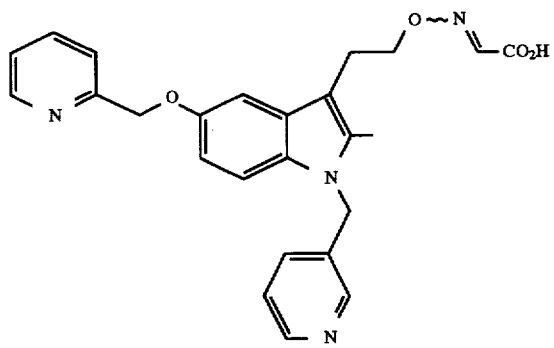

The title compound is prepared by reaction of glyoxylic acid-O-2-[1-(3-pyridylmethyl)-5-(pyrid-2-ylmethoxy)-2-methylindol-3-yl]ethyl oxime with trifluoroacetic acid to remove the t-BOC group followed by reaction of the indole intermediate with two equivalents of 3-pyridylmethyl chloride in the presence of a suitable base such as NaH to provide the intermediate glyoxylic acid 3-pyridyl ester-O-2-[1-(3-pyridylmethyl)-5-(pyrid-2-ylmethoxy)-2-methylindol-3-yl] ethyl oxime which is subsequently saponified.

EXAMPLE 42

Preparation of glyoxylic acid-O-2-[Z-5-fluoro-2-methyl-1-(4-methylsulfinylphenyl)methylene-1H-inden-3-yl]ethyl oxime

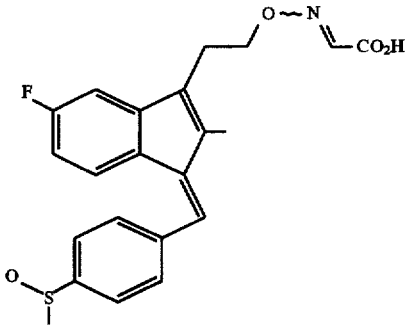

The title compound is prepared by the method of Example 1 to provide the key intermediate hydroxylamine, O-2-[Z-5-fluoro-2-methyl-1-(4-methylsulfinylphenyl)methylene-1H-inden-3-yl]ethyl hydroxylamine using sulindac instead of indomethacin.

EXAMPLE 43

Preparation of 3-oxopropionic acid-O-2-[Z-5-fluoro-2-methyl-1-(4-methylsulfinylphenyl)methylene-1H-inden-3-yl]ethyl oxime

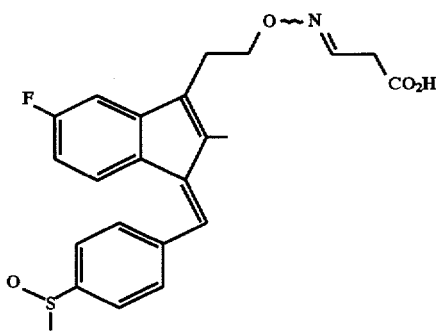

The title compound is prepared by reaction of O-2-[Z-5-fluoro-2-methyl-1-(4-methylsulfinylphenyl)methylene-1H-inden-3-yl]ethyl hydroxylamine with 3-oxopropionic acid by the method of Example 1.

EXAMPLE 44

Preparation of 2-oxopropionic acid-O-2-[Z-5-fluoro-2-methyl-1-(4-methylsulfinylphenyl)methylene-1H-inden-3-yl]ethyl oxime

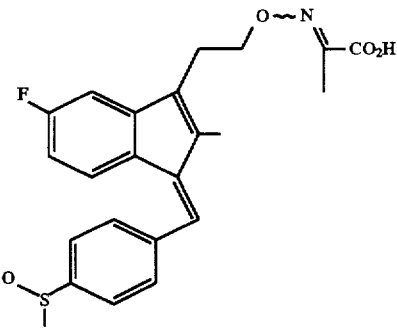

The title compound is prepared by reaction of O-2-[Z-5-fluoro-2-methyl-1-(4-methylsulfinylphenyl)methylene-1H-inden-3-yl]ethyl hydroxylamine with 2-oxopropionic acid by the method of Example 1.

EXAMPLE 45

Preparation of hydroxyacetaldehyde-O-2-[Z-5-fluoro-2-methyl-1-(4-methylsulfinylphenyl)methylene-1H-inden-3-yl]ethyl oxime

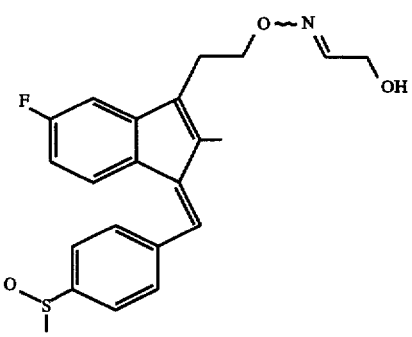

The title compound is prepared by reaction of O-2-[Z-5-fluoro-2-methyl-1-(4-methylsulfinylphenyl)methylene-1H-inden-3-yl]ethyl hydroxylamine with hydroxyacetaldehyde by the method of Example 1.

EXAMPLE 46

Preparation of 3-hydroxypropanal-O-2-[Z-5-fluoro-2-methyl-1-(4-methylsulfinylphenyl)methylene-1H-inden-3-yl]ethyl oxime

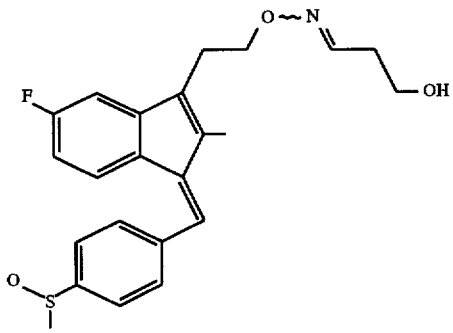

The title compound is prepared by reaction of O-2-[Z-5-fluoro-2-methyl-1-(4-methylsulfinylphenyl)methylene-1H-inden-3-yl]ethyl hydroxylamine with 3-hydroxypropanal by the method of Example 1.

EXAMPLE 47

Preparation of methoxyacetaldehyde-O-2-[Z-5-fluoro-2-methyl-1-(4-methylsulfinylphenyl)methylene-1H-inden-3-yl]ethyl oxime

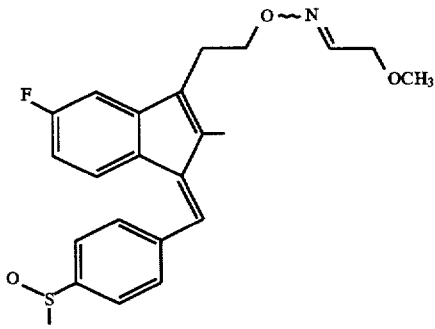

The title compound is prepared by reaction of O-2-[Z-5-fluoro-2-methyl-1-(4-methylsulfinylphenyl)methylene-1H-inden-3-yl]ethyl hydroxylamine with methoxyacetaldehyde by the method of Example 1.

EXAMPLE 48

Preparation of 3-methoxypropanal-O-2-[Z-5-fluoro-2-methyl-1-(4-methylsulfinylphenyl)methylene-1H-inden-3-yl]ethyl oxime

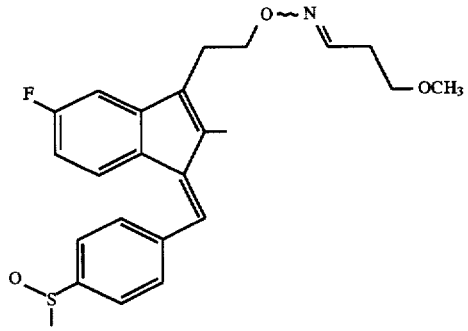

The title compound is prepared by reaction of O-2-[Z-5-fluoro-2-methyl-1-(4-methylsulfinylphenyl)methylene-1H-inden-3-yl]ethyl hydroxylamine with 3-methoxypropanal by the method of Example 1.

EXAMPLE 49

Preparation of phenoxyacetaldehyde-O-2-[Z-5-fluoro-2-methyl-1-(4-methylsulfinylphenyl)methylene-1H-inden-3-yl]ethyl oxime

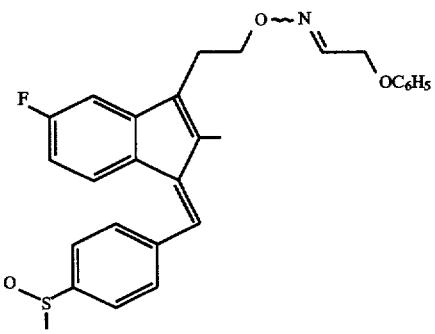

The title compound is prepared by reaction of O-2-[Z-5-fluoro-2-methyl-1-(4-methylsulfinylphenyl)methylene-1H-inden-3-yl]ethyl hydroxylamine with phenoxyacetaldehyde by the method of Example 1.

EXAMPLE 50

Preparation of phenoxypropanal-O-2-[Z-5-fluoro-2-methyl-1-(4-methylsulfinylphenyl)methylene-1H-inden-3-yl]ethyl oxime

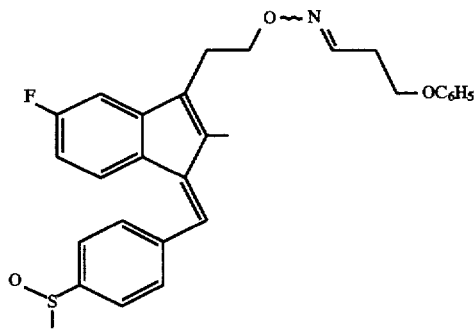

The title compound is prepared by reaction of O-2-[Z-5-fluoro-2-methyl-1-(4-methylsulfinylphenyl)methylene-1H-inden-3-yl]ethyl hydroxylamine with 3-phenoxypropanal by the method of Example 1.

EXAMPLE 51

Preparation of glyceracetaldehyde-O-2-[Z-5-fluoro-2-methyl-1-(4-methylsulfinylphenyl)methylene-1H-inden-3-yl]ethyl oxime

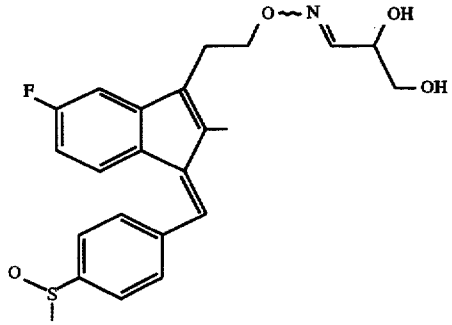

The title compound is prepared by reaction of O-2-[Z-5-fluoro-2-methyl-1-(4-methylsulfinylphenyl)methylene-1H-inden-3-yl]ethyl hydroxylamine with glyceracetaldehyde by the method of Example 1.

EXAMPLE 52

Preparation of 2,3-dimethoxypropanal-O-2-[Z-5-fluoro-2-methyl-1-(4-methylsulfinylphenyl)methylene-1H-inden-3-yl]ethyl oxime

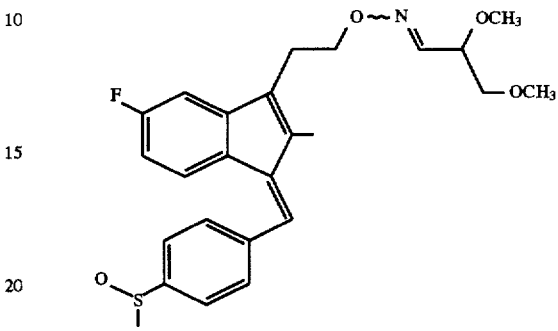

The title compound is prepared by reaction of O-2-[Z-5-fluoro-2-methyl-1-(4-methylsulfinylphenyl)methylene-1H-inden-3-yl]ethyl hydroxylamine with 2,3-dimethoxypropanal by the method of Example 1.

EXAMPLE 53

Preparation of glyoxal-O-2-[Z-5-fluoro-2-methyl-1-(4-methylsulfinylphenyl)methylene-1H-inden-3-yl] ethyl oxime

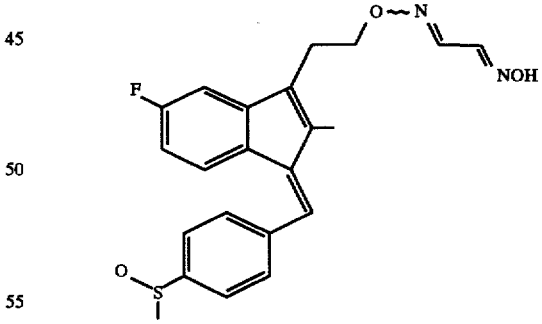

The title compound is prepared by reaction of O-2-[Z-5-fluoro-2-methyl-1-(4-methylsulfinylphenyl)methylene-1H-inden-3-yl]ethyl hydroxylamine with glyoxaloxime by the method of Example 1.

EXAMPLE 54

Preparation of O-methylglyoxal-O-2-[Z-5-fluoro-2-methyl-1-(4-methylsulfinylphenyl)methylene-1H-inden-3-yl]ethyl oxime

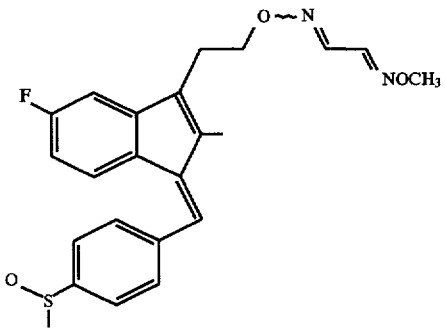

The title compound is prepared by reaction of O-2-[Z-5-fluoro-2-methyl-1-(4-methylsulfinylphenyl)methylene-1H-inden-3-yl]ethyl hydroxylamine with O-methylglyoxal by the method of Example 1.

EXAMPLE 55

Preparation of 5-formyltetrazole-O-2-[Z-5-fluoro-2-methyl-1-(4-methylsulfinylphenyl)methylene-1H-inden-3-yl]ethyl oxime

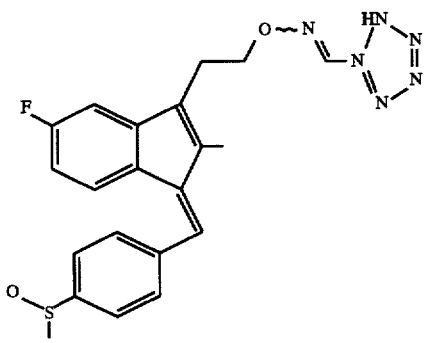

The title compound is prepared by reaction of O-2-[Z-5-fluoro-2-methyl-1-(4-methylsulfinylphenyl)methylene-1H-inden-3-yl]ethyl hydroxylamine with 5-formyltetrazole by the method of Example 1.

EXAMPLE 56

Preparation of O-2-[Z-5-fluoro-2-methyl-1-(4-methylthiophenyl)methylene-1H-inden-3-yl]ethyl hydroxylamine

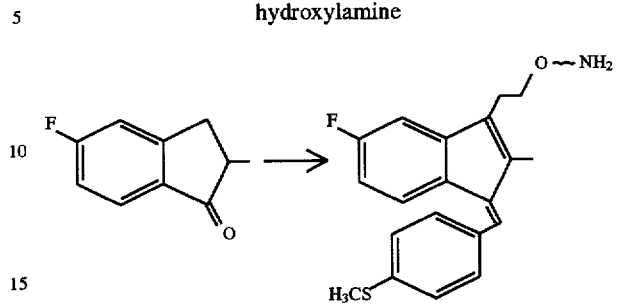

The title compound is prepared by Grignard reaction of 5-fluoro-2-methylindanone with 4-pyridylmethylmagnesium chloride to provide the intermediate adduct which is treated with glyoxalic acid under dehydrating Aldol conditions to provide Z-5-fluoro-2-methyl-1-(4-methylthiophenyl)methylene-1H-inden-3-yl] acetic acid which is converted to the hydroxylamine by the procedures described in Example 1.

EXAMPLE 57

Preparation of glyoxylic acid-O-2-[Z-5-fluoro-2-methyl-1-(4-methylthiophenyl)methylene-1H-inden-3-yl]ethyl oxime

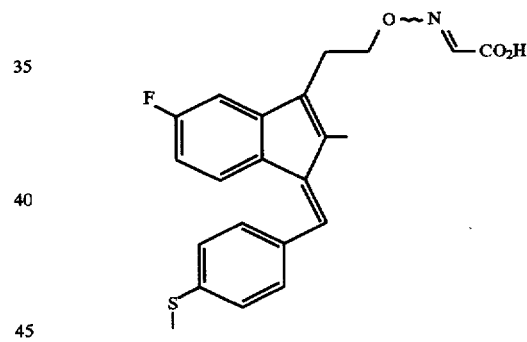

The title compound is prepared by reaction of O-2-[Z-5-fluoro-2-methyl-1-(4-methylthiophenyl)methylene-1H-inden-3-yl]ethyl hydroxylamine with glyoxylic acid.

EXAMPLE 58

Preparation of 3-oxopropionic acid-O-2-[Z-5-fluoro-2-methyl-1-(4-methylthiophenyl)methylene-1H-inden-3-yl]ethyl oxime

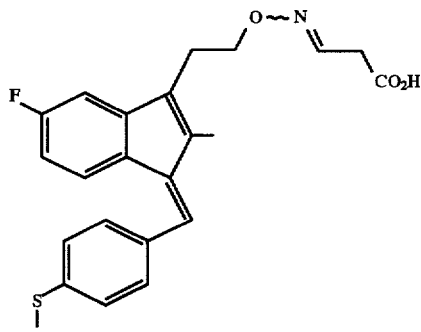

The title compound is prepared by reaction of O-2-[Z-5-fluoro-2-methyl-1-(4-methylthiophenyl)methylene-1H-inden-3-yl]ethyl hydroxylamine with 3-oxopropionic acid by the method of Example 1.

EXAMPLE 59

Preparation of 2-oxopropionic acid-O-2-[Z-5-fluoro-2-methyl-1-(4-methylthiophenyl)methylene-1H-inden-3-yl]ethyl oxime

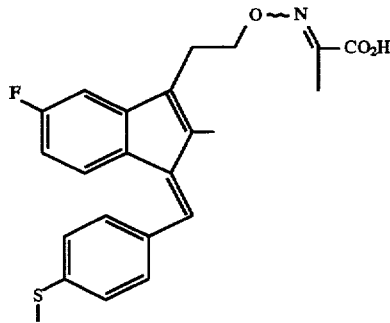

The title compound is prepared by reaction of O-2-[Z-5-fluoro-2-methyl-1-(4-methylthiophenyl)methylene-1H-inden-3-yl]ethyl hydroxylamine with 2-oxopropionic acid by the method of Example 1.

EXAMPLE 60

Preparation of hydroxyacetaldehyde-O-2-[Z-5-fluoro-2-methyl-1-(4-methylthiophenyl)methylene-1H-inden-3-yl]ethyl oxime

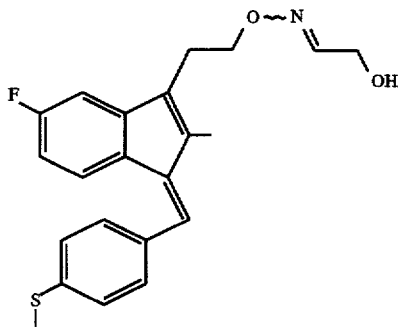

The title compound is prepared by reaction of O-2-[Z-5-fluoro-2-methyl-1-(4-methylthiophenyl)methylene-1H-inden-3-yl]ethyl hydroxylamine with hydroxyacetaldehyde by the method of Example 1.

EXAMPLE 61

Preparation of 3-hydroxypropanal-O-2-[Z-5-fluoro-2-methyl-1-(4-methylthiophenyl)methylene-1H-inden-3-yl]ethyl oxime

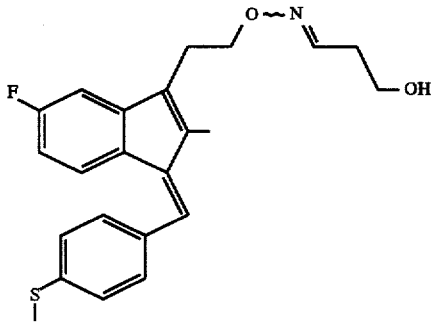

The title compound is prepared by reaction of O-2-[Z-5-fluoro-2-methyl-1-(4-methylthiophenyl)methylene-1H-inden-3-yl]ethyl hydroxylamine with 3-hydroxypropanal by the method of Example 1.

EXAMPLE 62

Preparation of methoxyacetaldehyde-O-2-[Z-5-fluoro-2-methyl-1-(4-methylsulfinylphenyl)methylene-1H-inden-3-yl]ethyl oxime

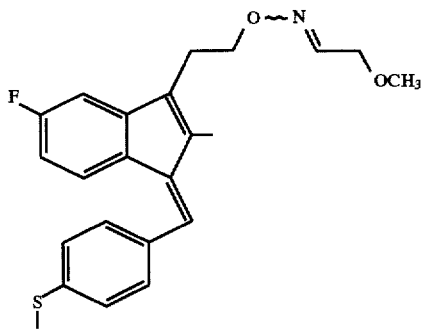

The title compound is prepared by reaction of O-2-[Z-5-fluoro-2-methyl-1-(4-methylthiophenyl)methylene-1H-inden-3-yl]ethyl hydroxylamine with methoxyacetaldehyde by the method of Example 1.

EXAMPLE 63

Preparation of 3-methoxypropanal-O-2-[Z-5-fluoro-2-methyl-1-(4-methylthiophenyl)methylene-1H-inden-3-yl]ethyl oxime

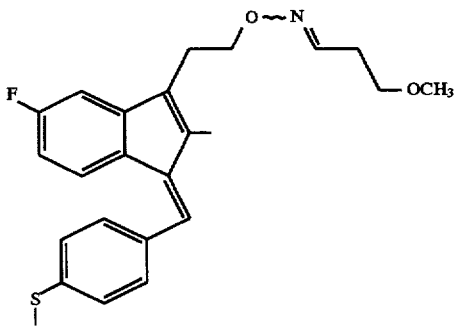

The title compound is prepared by reaction of O-2-[Z-5-fluoro-2-methyl-1-(4-methylthiophenyl)methylene-1H-inden-3-yl]ethyl hydroxylamine with 3-methoxypropanal by the method of Example 1.

EXAMPLE 64

Preparation of phenoxyacetaldehyde-O-2-[Z-5-fluoro-2-methyl-1-(4-methylthiophenyl)methylene-1H-inden-3-yl]ethyl oxime

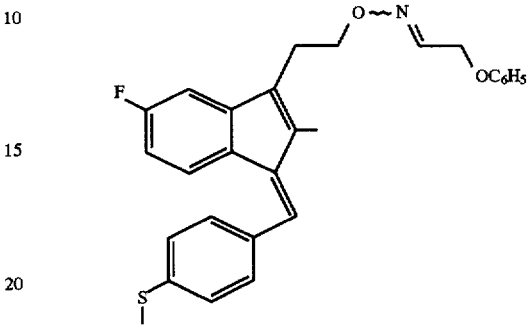

The title compound is prepared by reaction of O-2-[Z-5-fluoro-2-methyl-1-(4-methylthiophenyl)methylene-1H-inden-3-yl]ethyl hydroxylamine with phenoxyacetaldehyde by the method of Example 1.

EXAMPLE 65

Preparation of phenoxypropanal-O-2-[Z-5-fluoro-2-methyl-1-(4-methylthiophenyl)methylene-1H-inden-3-yl]ethyl oxime

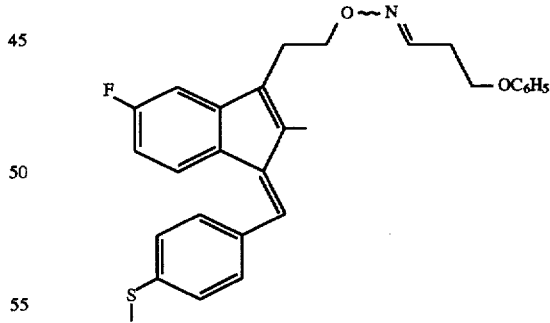

The title compound is prepared by reaction of O-2-[Z-5-fluoro-2-methyl-1-(4-methylthiophenyl)methylene-1H-inden-3-yl]ethyl hydroxylamine with 3-phenoxypropanal by the method of Example 1.

EXAMPLE 66

Preparation of glyceracetaldehyde-O-2-[Z-5-fluoro-2-methyl-1-(4-methylthiophenyl)methylene-1H-inden-3-yl]ethyl oxime

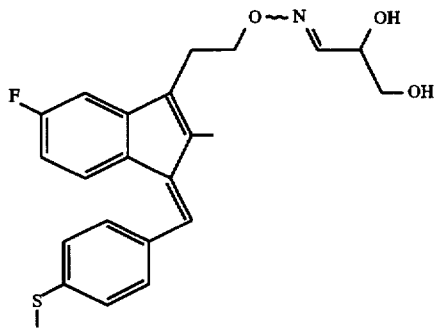

The title compound is prepared by reaction of O-2-[Z-5-fluoro-2-methyl-1-(4-methylthiophenyl)methylene-1H-inden-3-yl]ethyl hydroxylamine with glyceracetaldehyde by the method of Example 1.

EXAMPLE 67

Preparation of 2,3-dimethoxypropanal-O-2-[Z-5-fluoro-2-methyl-1-(4-methylthiophenyl)methylene-1H-inden-3-yl]ethyl oxime

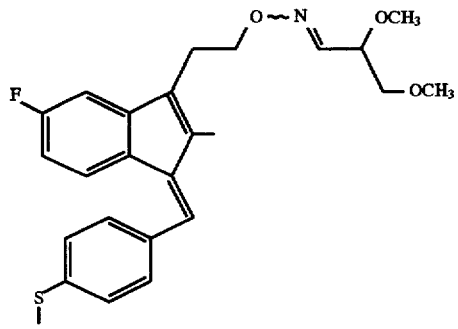

The title compound is prepared by reaction of O-2-[Z-5-fluoro-2-methyl-1-(4-methylthiophenyl)methylene-1H-inden-3-yl]ethyl hydroxylamine with 2,3-dimethoxypropanal by the method of Example 1.

EXAMPLE 68

Preparation of glyoxal-O-2-[Z-5-fluoro-2-methyl-1-(4-methylthiophenyl)methylene-1H-inden-3-yl]ethyl oxime

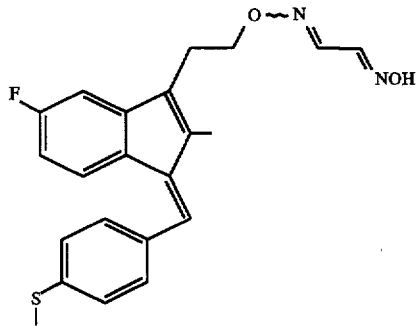

The title compound is prepared by reaction of O-2-[Z-5-fluoro-2-methyl-1-(4-methylthiophenyl)methylene-1H-inden-3-yl]ethyl hydroxylamine with glyoxal by the method of Example 1.

EXAMPLE 69

Preparation of O-methylglyoxal-O-2-[Z-5-fluoro-2-methyl-1-(4-methylthiophenyl)methylene-1H-inden-3-yl]ethyl oxime

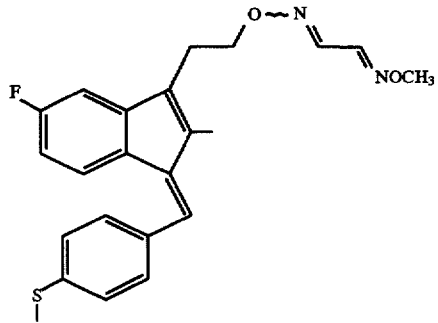

The title compound is prepared by reaction of O-2-[Z-5-fluoro-2-methyl-1-(4-methylthiophenyl)methylene-1H-inden-3-yl]ethyl hydroxylamine with O-methylglyoxal by the method of Example 1.

EXAMPLE 70

Preparation of 5-formyltetrazole-O-2-[Z-5-fluoro-2-methyl-1-(4-methylthiophenyl)methylene-1H-inden-3-yl]ethyl oxime

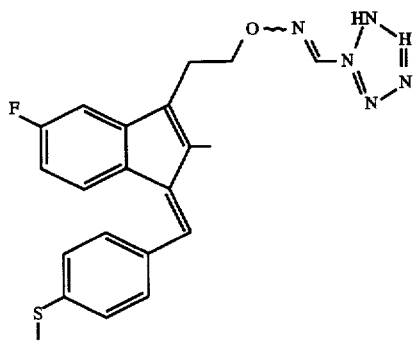

The title compound is prepared by reaction of O-2-[Z-5-fluoro-2-methyl-1-(4-methylthiophenyl)methylene-1H-inden-3-yl]ethyl hydroxylamine with 5-formyltetrazole by the method of Example 1.

EXAMPLE 71

Preparation of O-2-[Z-5-fluoro-2-methyl-1-(4-pyridyl)methylene-1H-inden-3-yl]ethyl hydroxylamine

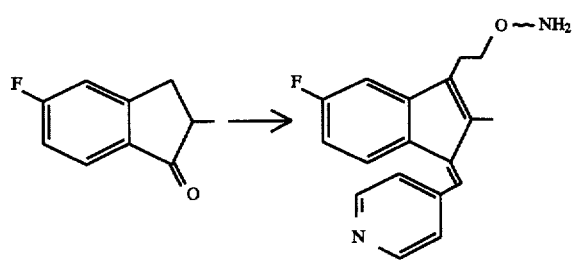

The title compound is prepared by Grignard reaction of 5-fluoro-2-methylindanone with 4-pyridylmethylmagnesium chloride to provide the intermediate adduct which is treated with glyoxalic acid under dehydrating aldol conditions to provide Z-5-fluoro-2-methyl-1-(4-pyridyl)methylene-1H-inden-3-yl]acetic acid which is converted to the hydroxylamine by the procedures described in Example 1.

EXAMPLE 72

Preparation of glyoxylic acid-O-2-[Z-5-fluoro-2-methyl-1-(4-pyridyl)methylene-1H-inden-3-yl]ethyl oxime

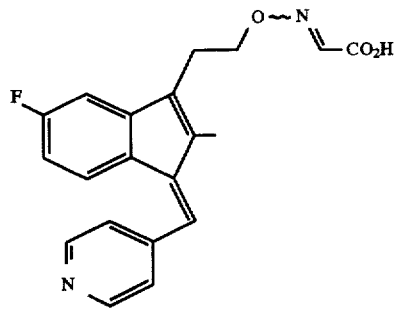

The title compound is prepared by reaction of O-2-[Z-5-fluoro-2-methyl-1-(4-pyridyl)methylene-1H-inden-3-yl]ethyl hydroxylamine with glyoxylic acid.

EXAMPLE 73

Preparation of 3-oxopropionic acid-O-2-[Z-5-fluoro-2-methyl-1-(4-pyridyl)methylene-1H-inden-3-yl]ethyl oxime

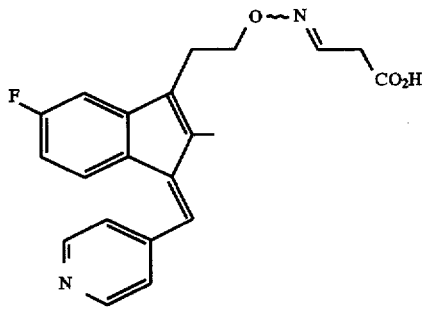

The title compound is prepared by reaction of O-2-[Z-5-fluoro-2-methyl-1-(4-pyridyl)methylene-1H-inden-3-yl]ethyl hydroxylamine with 3-oxopropionic acid by the method of Example 1.

EXAMPLE 74

Preparation of 2-oxopropionic acid-O-2-[Z-5-fluoro-2-methyl-1-(4-pyridyl)methylene-1H-inden-3-yl]ethyl oxime

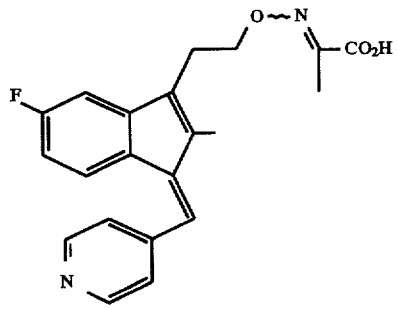

The title compound is prepared by reaction of O-2-[Z-5-fluoro-2-methyl-1-(4-pyridyl)methylene-1H-inden-3-yl]ethyl hydroxylamine with 2-oxopropionic acid by the method of Example 1.

EXAMPLE 75

Preparation of hydroxyacetaldehyde-O-2-[Z-5-fluoro-2-methyl-1-(4-pyridyl)methylene-1H-inden-3-yl]ethyl oxime

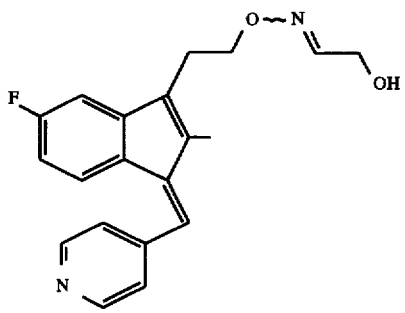

The title compound is prepared by reaction of O-2-[Z-5-fluoro-2-methyl-1-(4-pyridyl)methylene-1H-inden-3-yl]ethyl hydroxylamine with hydroxyacetaldehyde by the method of Example 1.

EXAMPLE 76

Preparation of 3-hydroxypropanal-O-2-[Z-5-fluoro-2-methyl-1-(4-pyridyl)methylene-1H-inden-3-yl]ethyl oxime

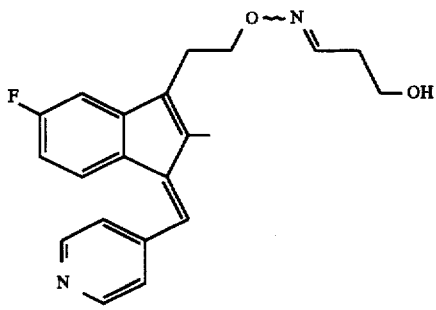

The title compound is prepared by reaction of O-2-[Z-5-fluoro-2-methyl-1-(4-pyridyl)methylene-1H-inden-3-yl]ethyl hydroxylamine with 3-hydroxypropanal by the method of Example 1.

EXAMPLE 77

Preparation of methoxyacetaldehyde-O-2-[Z-5-fluoro-2-methyl-1-(4-pyridyl)methylene-1H-inden-3-yl]ethyl oxime

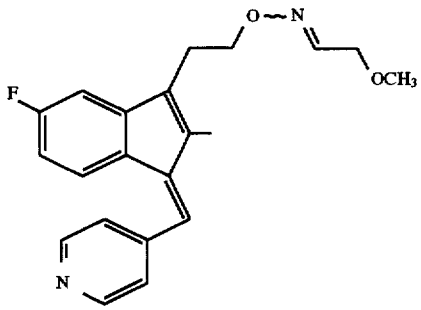

The title compound is prepared by reaction of O-2-[Z-5-fluoro-2-methyl-1-(4-pyridyl)methylene-1H-inden-3-yl]ethyl hydroxylamine with methoxyacetaldehyde by the method of Example 1.

EXAMPLE 78

Preparation of 3-methoxypropanal-O-2-[Z-5-fluoro-2-methyl-1-(4-pyridyl)methylene-1H-inden-3-yl]ethyl oxime

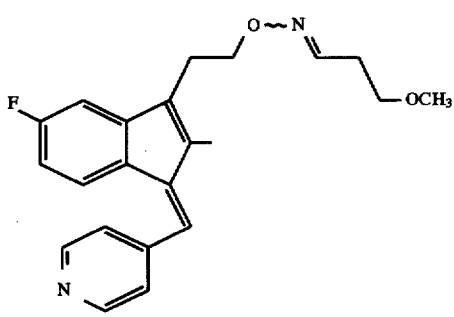

The title compound is prepared by reaction of O-2-[Z-5-fluoro-2-methyl-1-(4-pyridyl)methylene-1H-inden-3-yl]ethyl hydroxylamine with 3-methoxypropanal by the method of Example 1.

EXAMPLE 79

Preparation of phenoxyacetaldehyde-O-2-[Z-5-fluoro-2-methyl-1-(4-pyridyl)methylene-1H-inden-3-yl]ethyl oxime

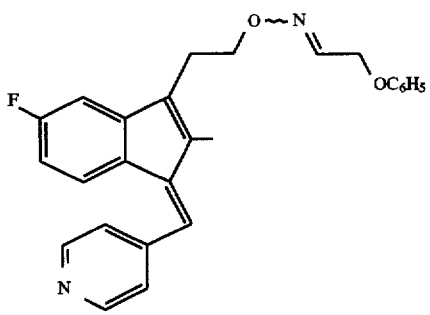

The title compound is prepared by reaction of O-2-[Z-5-fluoro-2-methyl-1-(4-pyridyl)methylene-1H-inden-3-yl]ethyl hydroxylamine with phenoxyacetaldehyde by the method of Example 1.

EXAMPLE 80

Preparation of phenoxypropanal-O-2-[Z-5-fluoro-2-methyl-1-(4-pyridyl)methylene-1H-inden-3-yl]ethyl oxime

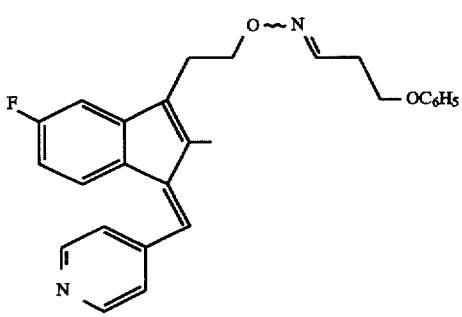

The title compound is prepared by reaction of O-2-[Z-5-fluoro-2-methyl-1-(4-pyridyl)methylene-1H-inden-3-yl] ethyl hydroxylamine with 3-phenoxypropanal by the method of Example 1.

EXAMPLE 81

Preparation of glyceracetaldehyde-O-2-[Z-5-fluoro-2-methyl-1-(4-pyridyl)methylene-1H-inden-3-yl]ethyl oxime

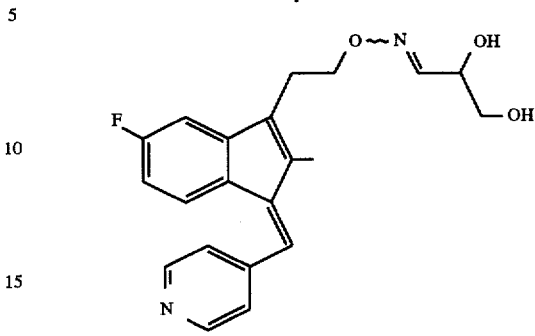

The title compound is prepared by reaction of O-2-[Z-5-fluoro-2-methyl-1-(4-pyridyl)methylene-1H-inden-3-yl] ethyl hydroxylamine with glyceracetaldehyde by the method of Example 1.

EXAMPLE 82

Preparation of 2,3-dimethoxypropanal-O-2-[Z-5-fluoro-2-methyl-1-(4-pyridyl)methylene-1H-inden-3-yl]ethyl oxime

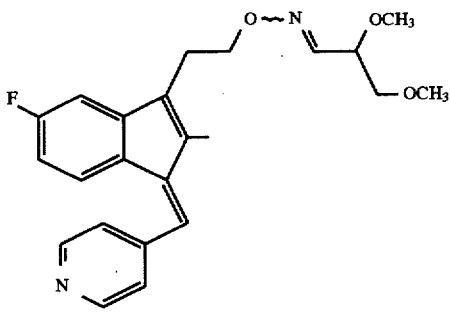

The title compound is prepared by reaction of O-2-[Z-5-fluoro-2-methyl-1-(4-pyridyl)methylene-1H-inden-3-yl] ethyl hydroxylamine with 2,3-dimethoxypropanal by the method of Example 1.

EXAMPLE 83

Preparation of glyoxal-O-2-[Z-5-fluoro-2-methyl-1-(4-pyridyl)methylene-1H-inden-3-yl]ethyl oxime

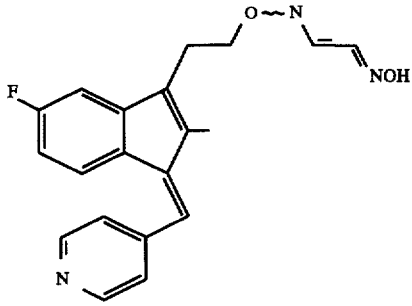

The title compound is prepared by reaction of O-2-[Z-5-fluoro-2-methyl-1-(4-pyridyl)methylene-1H-inden-3-yl]ethyl hydroxylamine with glyoxal by the method of Example 1.

EXAMPLE 84

Preparation of O-methylglyoxal-O-2-[Z-5-fluoro-2-methyl-1-(4-pyridyl)methylene-1H-inden-3-yl]ethyl oxime

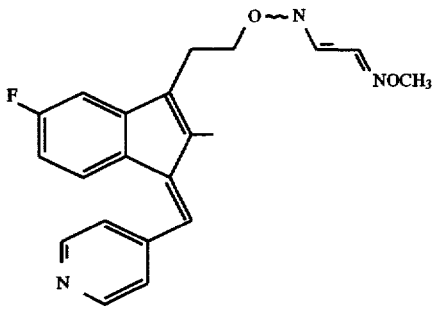

The title compound is prepared by reaction of O-2-[Z-5-fluoro-2-methyl-1-(4-pyridyl)methylene-1H-inden-3-yl]ethyl hydroxylamine with O-methylglyoxal by the method of Example 1.

EXAMPLE 85

Preparation of 5-formyltetrazole-O-2-[Z-5-fluoro-2-methyl-1-(4-pyridyl)methylene-1H-inden-3-yl]ethyl oxime

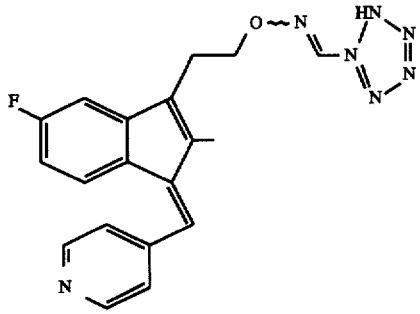

The title compound is prepared by reaction of O-2-[Z-5-fluoro-2-methyl-1-(4-pyridyl)methylene-1H-inden-3-yl]ethyl hydroxylamine with 5-formyltetrazole by the method of Example 1.

What is claimed is:

1. A compound of the formula

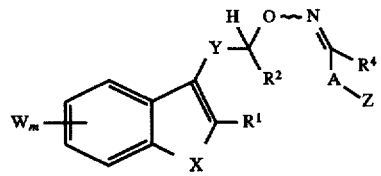

or a pharmaceutically acceptable salt thereof wherein m is an integer of one to three, inclusive;

W is independently selected at each occurrence from the group consisting of a) halogen;
b) alkyl of one to six carbon atoms;
c) haloalkyl of one to six carbon atoms; and
d) alkoxy of one to six carbon atoms;

X is selected from the group consisting of

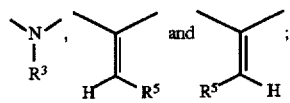

Y is absent or is alkylene of one to six carbon atoms;

A is absent or is selected from the group consisting of a) unsubstituent alkylene of one to six carbon atoms;
b) alkylene of one to six carbon atoms substituted with one or two substituents independently selected from the group selected from —OH and alkoxy of one to six carbon atoms;
c) unsubstituted alkenylene;
d) alkylene substituted with one or two alkoxy groups one to six carbon atoms;
e) cycloalkylene of three to eight carbon atoms;
f) cycloalkylene of three to eight carbon atoms substituted with one or two substituents independently selected from the group consisting of hydroxy and alkoxy of one to six carbon atoms; and
g) a phenylene ring substituted with one to three groups independently selected from the group consisting of hydroxy, alkoxy of one to six carbon atoms and alkyl of one to six carbon atoms;

Z is selected from the group consisting of a) hydrogen;
b) —C(O)M;
c) hydroxy;
d) alkoxy of one to six carbon atoms;
e) unsubstituted phenoxy;
f) phenoxy substituted with one or two substituents independently selected from alkyl of one to six carbon atoms and alkoxy of one to six carbon atoms;
g) —CH=NOH; and
h) —CH=NOR where R is alkyl of one to six carbon atoms and M is selected from the group consisting of hydroxy or a pharmaceutically acceptable cation thereof; alkoxy of one to six carbon atoms; —NR$^7$R$^8$;

R$^1$ is selected from the group consisting of a) hydrogen,
b) hydroxy,
c) alkyl of one to six carbon atoms, and
d) hydroxyalkyl of one to six carbon atoms;

R$^2$ is selected from the group consisting of a) hydrogen;
b) alkyl of one to six carbon atoms;
c) unsubstituted phenyl;
d) phenyl substituted with one to three groups independently selected from the group consisting of halogen, alkyl of one to six carbon atoms, haloalkyl of one to six carbon atoms, and alkoxy of one to six carbon atoms;
e) unsubstituted phenylalkyl in which the alkyl portion is of one to six carbon atoms; and
f) phenylalkyl in which the alkyl portion is of one to six carbon atoms and the phenyl ring is substituted with one to three groups independently selected from the group consisting of halogen, alkyl of one to six carbon atoms, haloalkyl of one to six carbon atoms, and alkoxy of one to six carbon atoms;

$R^3$ is selected from the group consisting of
a) unsubstituted benzoyl;
b) benzoyl substituted with one or two substituents independently selected from the group consisting of halogen, alkyl of one to six carbon atoms, and alkoxy of one to six carbon atoms;
c) unsubstituted benzyl;
d) benzyl substituted with one or two substituents independently selected from the group consisting of halogen, alkyl of one to six carbon atoms, and alkoxy of one to six carbon atoms;
e) alkoxycarbonyl of two to six carbon atoms;
f) unsubstituted phenyl; and
g) phenyl substituted with one or two substituents independently selected from the group consisting of halogen, alkyl of one to six carbon atoms, and alkoxy of one to six carbon atoms, —SR, and —S(O)R where R is alkyl of one to six carbon atoms;

$R^4$ is selected from the group consisting of
a) hydrogen;
b) alkyl of one to six carbon atoms;
c) unsubstituted phenyl; and
d) phenyl substituted with one to three substituents independently selected from the group consisting of alkyl of one to six carbon atoms, and alkoxy of one to six carbon atoms;

$R^5$ is selected from
a) unsubstituted phenyl; and
b) phenyl substituted with one or two substituents independently selected from the group consisting of halogen, alkyl of one to six carbon atoms, alkoxy of one to six carbon atoms, —SR, and —S(O)R where R is alkyl of one to six carbon atoms;

$R^7$ and $R^8$ are independently selected from the group consisting of
a) hydrogen,
b) alkyl of one to six carbon atoms,
c) hydroxyalkyl of one to six carbon atoms and
d) hydroxy;

with the proviso that $R^7$ and $R^8$ may not both be hydroxy.

2. A compound as defined by claim 1 having the structure

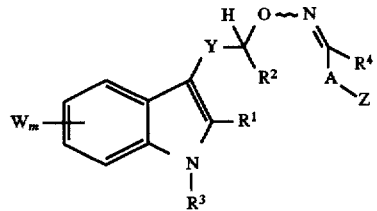

or a pharmaceutically acceptable salt thereof where W, m, $R^1$, $R^2$, $R^3$, Y, A and Z are as defined therein.

3. A compound as defined by claim 1 selected from the group consisting of compounds having the structure

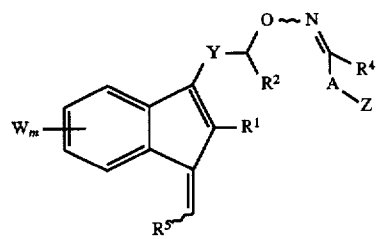

or a pharmaceutically acceptable salt thereof wherein W, m, $R^1$, $R^2$, $R^5$, Y, A and Z are as defined therein.

4. A compound as defined by claim 2 wherein $R^1$ is alkyl of one to six carbon atoms and Y is methylene.

5. A compound as defined by claim 3 wherein $R^1$ is alkyl of one to six carbon atoms and Y is methylene.

6. A compound as defined by claim 4 selected from the group consisting of
glyoxylic acid-O-[2-(4-chlorobenzoyl-5-methoxy-2-methylindol-3-yl)ethyl] oxime;
[2-thienylglyoxylic acid-O-[2-(4-chlorobenzoyl-5-methoxy-2-methylindol-3-yl)ethyl] oxime;]
2-phenylglyoxylic acid-O-[2-(4-chlorobenzoyl-5-methoxy-2-methylindol-3-yl)ethyl]oxime;
4-carboxyphenyl methyl ketone-O-[2-(4-chlorobenzoyl-5-methoxy-2-methylindol-3-yl)ethyl] oxime;
2-oxohexanoic acid-O-[2-(4-chlorobenzoyl-5-methoxy-2-methylindol-3-yl)ethyl]oxime;
4-oxopent-2-enoic acid-2-O-[2-(4-chlorobenzoyl-5-methoxy-2-methylindol-3-yl)ethyl] oxime;
glyceraldehyde-O-[2-(1-(4-chlorobenzoyl)-5-methoxy-2-methylindol-3-yl)ethyl]oxime;
[(2,3,5,6-tetrahydropyran-4-one-O-[2-(4-chlorophenylmethyl-5-methoxy-2-methylindol-3-yl)ethyl]oxime;
(2,3,5,6-tetrahydrothiopyran-4-one-O-[2-(4-chlorophenylmethyl-5-methoxy-2-methylindol-3-yl)ethyl]oxime;]
glyoxylic acid-O-[2-(4-chlorophenylmethyl-5-methoxy-2-methylindol-3-yl)ethyl]oxime;
3-oxopropionic acid-O-[2-(4-chlorophenylmethyl-5-methoxy-2-methylindol-3-yl)ethyl]oxime;
hydroxyacetaldehyde-O-[2-(4-chlorophenylmethyl-5-methoxy-2-methylindol-3-yl)ethyl]oxime;
3-hydroxpropanal-O-[2-(4-chlorophenylmethyl-5-methoxy-2-methylindol-3-yl)ethyl]oxime;
methoxyacetaldehyde-O-[2-(4-chlorophenylmethyl-5-methoxy-2-methylindol-3-yl)ethyl]oxime;
3-methoxypropanal-O-[2-(4-chlorophenylmethyl-5-methoxy-2-methylindol-3-yl)ethyl]oxime;
phenoxyacetaldehyde-O-[2-(4-chlorophenylmethyl-5-methoxy-2-methylindol-3-yl)ethyl]oxime;
3-phenoxypropanal-O-[2-(4-chlorophenylmethyl-5-methoxy-2-methylindol-3-yl)ethyl]oxime;
2,3-dimethoxypropanal-O-[2-(4-chlorophenylmethyl-5-methoxy-2-methylindol-3-yl)ethyl]oxime; and
glyoxal-O-[2-(4-chlorophenylmethyl-5-methoxy-2-methylindol-3-yl)ethyl]oxime;
[5-formyltetrazole-O-[2-(4-chlorophenylmethyl-5-methoxy-2-methylindol-3-yl)ethyl]oxime;
glyoxylic acid-O-2-[1-(t-butoxycarbonyl)-5-(thiazol-2-ylmethoxy)-2-methylindol-3-yl)ethyloxime;
glyoxylic acid-O-2-[1-(3-pyridylmethyl)-5-(thiazol-2-ylmethoxy)-2-methylindol-3-yl)ethyloxime;
glyoxylic acid-O-2-[1-(t-butoxycarbonyl)-5-(benzothiazol-2-ylmethoxy)-2-methylindol-3-yl]ethyloxime;

glyoxylic acid-O-2-[1-(3-pyridylmethyl)-5-(benzothiazol-2-ylmethoxy)-2-methylindol-3-yl]ethyloxime;

glyoxylic acid-O-2-[1-(t-butoxycarbonyl)-5-(quinol-2-ylmethoxy)-2-methylindol-3-yl]ethyloxime;

glyoxylic acid-O-2-[1-(3-pyridylmethyl)-5-(quinol-2-ylmethoxy)-2-methylindol-3-yl]ethyloxime;

glyoxylic acid-O-2-[1[(t-butoxycarbonyl)-5-(pyrid-2-ylmethoxy)-2-methylindol-3-yl]ethyloxime; and glyoxylic acid-O-2-[1-(3-pyridylmethyl)-5-(quinol-2-ylmethoxy)-2-methylindol-3-yl]ethyloxime;]

or a pharmaceutically acceptable salt thereof.

7. A compound as defined by claim 5 selected from the group consisting of glyoxylic acid-O-2-[Z-5-fluoro-2-methyl-1-(4-methylsulfinylphenyl)methylene-1H-inden-3-yl]ethyloxime;

3-oxopropionic acid-O-2-[Z-5-fluoro-2-methyl-1-(4-methylsulfinylphenyl)methylene-1H-inden-3-yl]ethyloxime;

2-oxopropionic acid-O-2-[Z-5-fluoro-2-methyl-1-(4-methylsulfinylphenyl)methylene-1H-inden-3-yl]ethyloxime;

hydroxyacetaldehyde-O-2-[Z-5-fluoro-2-methyl-1-(4-methylsulfinylphenyl)methylene-1H-inden-3-yl]ethyloxime;

3-hydroxypropanal-O-2-[Z-5-fluoro-2-methyl-1-(4-methylsulfinylphenyl)methylene-1H-inden-3-yl]ethyloxime;

methoxyacetaldehyde-O-2-[Z-5-fluoro-2-methyl-1-(4-methylsulfinylphenyl)methylene-1H-inden-3-yl]ethyloxime;

3-methoxypropanal-O-2-[Z-5-fluoro-2-methyl-1-(4-methylsulfinylphenyl)methylene-1H-inden-3-yl]ethyloxime;

phenoxyacetaldehyde-O-2-[Z-5-fluoro-2-methyl-1-(4-methylsulfinylphenyl)methylene-1H-inden-3-yl]ethyloxime;

phenoxypropanal-O-2-[Z-5-fluoro-2-methyl-1-(4-methylsulfinylphenyl)methylene-1H-inden-3-yl]ethyloxime;

glyceracetaldehyde-O-2-[Z-5-fluoro-2-methyl-1-(4-methylsulfinylphenyl)methylene-1H-inden-3-yl]ethyloxime;

2,3-dimethoxypropanal-O-2-[Z-5-fluoro-2-methyl-1-(4-methylsulfinylphenyl)methylene-1H-inden-3-yl]ethyloxime;

glyoxal-O-2-[Z-5-fluoro-2-methyl-1-(4-methylsulfinylphenyl)-methylene-1H-inden-3-yl]ethyloxime;

O-methylglyoxal-O-2-[Z-5-fluoro-2-methyl-1-(4-methylsulfinylphenyl)methylene-1H-inden-3-yl]ethyloxime;

glyoxylic acid-O-2-[Z-5-fluoro-2-methyl-1-(4-methylthiophenyl)-methylene-1H-inden-3-yl]ethyloxime;

3-oxopropionic acid-O-2-[Z-5-fluoro-2-methyl-1-(4-methylthiophenyl)methylene-1H-inden-3-yl]ethyloxime;

2-oxopropionic acid-O-2-[Z-5-fluoro-2-methyl-1-(4-methylthiophenyl)methylene-1H-inden-3-yl]ethyloxime;

hydroxyacetaldehyde-O-2-[Z-5-fluoro-2-methyl-1-(4-methylthiophenyl)methylene-1H-inden-3-yl]ethyloxime;

3-hydroxypropanal-O-2-[Z-5-fluoro-2-methyl-1-(4-methylthiophenyl)methylene-1H-inden-3-yl]ethyloxime;

methoxyacetaldehyde-O-2-[Z-5-fluoro-2-methyl-1-(4-methylthiophenyl)methylene-1H-inden-3-yl]ethyloxime;

3-methoxypropanal-O-2-[Z-5-fluoro-2-methyl-1-(4-methylthiophenyl)methylene-1H-inden-3-yl]ethyloxime;

phenoxyacetaldehyde-O-2-[Z-5-fluoro-2-methyl-1-(4-methylthiophenyl)methylene-1H-inden-3-yl]ethyloxime;

phenoxypropanal-O-2-[Z-5-fluoro-2-methyl-1-(4-methylthiophenyl)methylene-1H-inden-3-yl]ethyloxime;

glyceracetaldehyde-O-2-[Z-5-fluoro-2-methyl-1-(4-methylthiophenyl)methylene-1H-inden-3-yl]ethyloxime;

2,3-dimethoxypropanal-O-2-[Z-5-fluoro-2-methyl-1-(4-methylthiophenyl)methylene-1H-inden-3-yl]ethyloxime;

glyoxal-O-2-[Z-5-fluoro-2-methyl-1-(4-methylthiophenyl)-methylene-1H-inden-3-yl]ethyloxime; and O-methylglyoxal-O-2-[Z-5-fluoro-2-methyl-1-(4-methylthiophenyl)methylene-1H-inden-3-yl]ethyloxime;

or a pharmaceutically acceptable salt thereof.

8. A composition for inhibiting prostaglandin synthesis in a mammal comprising an effective amount of a compound as defined by claim 1 in combination with a pharmaceutically acceptable carrier.

9. A method of inhibiting prostaglandin synthesis in a mammal in need of such treatment comprising administering a therapeutically effective amount of a compound as defined by claim 1 or a pharmaceutically acceptable salt thereof.

* * * * *

UNITED STATES PATENT AND TRADEMARK OFFICE
CERTIFICATE OF CORRECTION

PATENT NO. : 5,756,531
DATED : May 26, 1998
INVENTOR(S) : Brooks et al.

It is certified that error appears in the above-identified patent and that said Letters Patent is hereby corrected as shown below:

Column 62, Delete lines 22-23; 34-39; 60-67

Column 63, Delete lines 1-10

Signed and Sealed this

First Day of December, 1998

Attest:

BRUCE LEHMAN

*Attesting Officer*              *Commissioner of Patents and Trademarks*